United States Patent
Song et al.

(10) Patent No.: US 11,684,780 B2
(45) Date of Patent: Jun. 27, 2023

(54) CLOSED-LOOP MULTI-CHANNEL ASYNCHRONOUS NEUROSTIMULATOR TO MIMIC NEURAL CODE FOR COGNITIVE PROSTHESIS

(71) Applicant: University of Southern California, Los Angeles, CA (US)

(72) Inventors: Dong Song, Walnut, CA (US); Theodore W. Berger, Rancho Palos Verdes, CA (US); Sahar Elyahoodayan, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 16/656,478

(22) Filed: Oct. 17, 2019

(65) Prior Publication Data

US 2020/0121929 A1 Apr. 23, 2020

Related U.S. Application Data

(60) Provisional application No. 62/747,012, filed on Oct. 17, 2018.

(51) Int. Cl.
*A61N 1/36* (2006.01)

(52) U.S. Cl.
CPC ..... *A61N 1/36128* (2013.01); *A61N 1/36125* (2013.01); *A61N 1/36082* (2013.01)

(58) Field of Classification Search
CPC ............ A61N 1/36128; A61N 1/36125; A61N 1/36082
See application file for complete search history.

(56) References Cited

U.S. PATENT DOCUMENTS

| | | | |
|---|---|---|---|
| 2014/0200638 A1* | 7/2014 | Chow | A61N 1/36142 607/116 |
| 2014/0275847 A1* | 9/2014 | Perryman | A61B 5/0205 600/301 |
| 2015/0018913 A1* | 1/2015 | Leven | A61N 1/0551 607/116 |
| 2015/0164354 A1* | 6/2015 | Parker | A61N 1/36146 600/554 |

* cited by examiner

*Primary Examiner* — Paula J Stice
(74) *Attorney, Agent, or Firm* — Snell & Wilmer L.L.P.

(57) ABSTRACT

A method for providing stimulation of living tissue may include generating electrical pulses onto multiple output channels to a plurality of electrodes each corresponding to one of the multiple output channels. The method may also include disconnecting the plurality of electrodes from recording amplifiers during a stimulation. Additionally, the method may include shorting, after each stimulation before recording is resumed, inputs of the recording amplifiers to ground to suppress ringing in the recording system.

16 Claims, 23 Drawing Sheets

CLOSED-LOOP MULTI-CHANNEL ASYNCHRONOUS NEUROSTIMULATOR TO MIMIC NEURAL CODE FOR COGNITIVE PROSTHESIS

CROSS-REFERENCE TO RELATED APPLICATIONS

This application claims priority to, and the benefit of, U.S. Prov. Pat. Appl., Ser. No. 62/747,012, entitled "CLOSED-LOOP MULTI-CHANNEL ASYNCHRONOUS NEUROSTIMULATOR TO MIMIC NEURAL CODE FOR COGNITIVE PROSTHESIS," filed on Oct. 17, 2018, the entirety of which is incorporated herein for all purposes by this reference.

STATEMENT AS TO FEDERALLY SPONSORED RESEARCH

This invention was made with government support under contract number CBET-1343193 awarded by the National Science Foundation (NSF). The government has certain rights in this invention.

FIELD

The present disclosure relates generally to neurostimulation and, more particularly, to neurostimulation to mimic neural code for cognitive prosthesis.

BACKGROUND

Neural interface technology has made much progress in recent years aiming to advance basic neuroscience research and provide therapies to patients with neurological damages or diseases. Researchers have been using neural interfaces as a tool to record and manipulate neural circuits to study neural correlates of sensory, motor, and cognitive functions. In the clinic, deep brain stimulation (DBS) has provided treatments to various neurological disorders such as epilepsy, depression, Parkinson's disease, memory loss, and Tourette's syndrome. In neural prosthesis applications, neural interfaces have been used to convert sensory input signals to neural stimulations as in cochlea prostheses and retinal prostheses. In neural prosthesis applications, neural interfaces have also been used to decode motor cortical output signals into movements as in motor prostheses.

SUMMARY

A system for providing stimulation of living tissue is provided. The system includes a stimulation generator configured to generate electrical pulses onto multiple output channels. Additionally, the system includes a plurality of electrodes each corresponding to one of the multiple output channels. The system also includes a first plurality of switches each located between one of the multiple output channels and a corresponding electrode of the plurality of electrodes.

A method for providing stimulation of living tissue is provided. The method includes generating electrical pulses onto multiple output channels to a plurality of electrodes each corresponding to one of the multiple output channels. Additionally, the method includes disconnecting the plurality of electrodes from recording amplifiers during a stimulation. The method also includes shorting, after each stimulation before recording is resumed, inputs of the recording amplifiers to ground to suppress ringing in the recording system.

A system for providing stimulation of living tissue is provided. The system includes means for generating electrical pulses onto multiple output channels to a plurality of electrodes each corresponding to one of the multiple output channels. Additionally, the system includes means for disconnecting the plurality of electrodes from recording amplifiers during a stimulation. The system also includes mean for shorting, after each stimulation before recording is resumed, inputs of the recording amplifiers to ground to suppress ringing in the recording system.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

Figure 1:
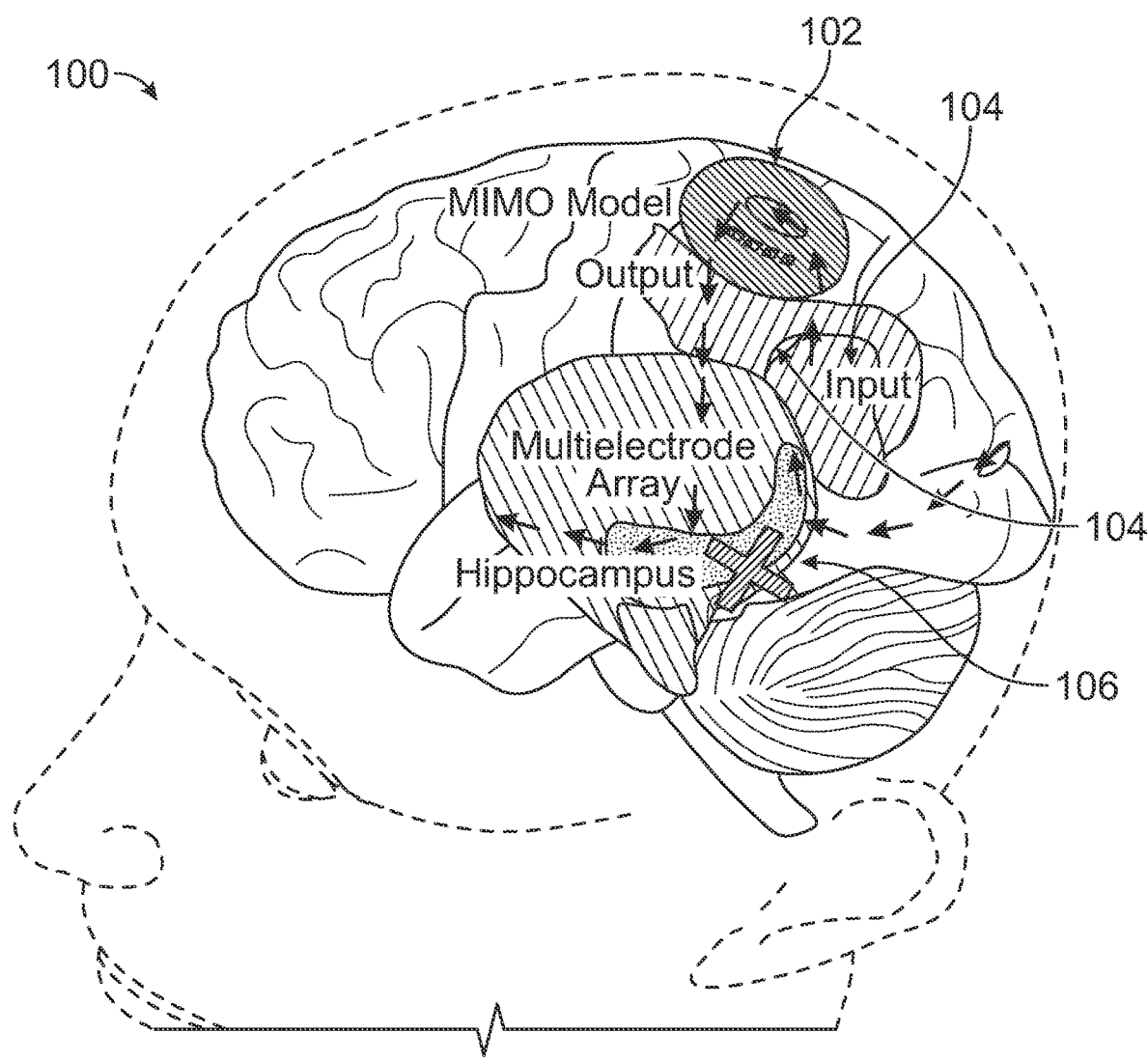
FIG. 1 is a diagram illustrating a representation of a cognitive prosthesis.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

The systems, devices, and methods described herein generally relate to a closed-loop multi-channel asynchronous neurostimulator that may mimic neural code for a cognitive prosthesis. A cognitive prothesis may be an electronic computational device that may extend the capability of human cognition or sense perception, e.g., a system that may support and augment the cognitive abilities of a user. For example, various hardware, software, or both may be used with an embedded system design to form a closed loop neurostimulator for generating neural code-like, multi-channel, asynchronous electrical stimulation pulses. Such a stimulator may be used as an output unit of a cortical prosthesis that aims to restore cognitive functions by reinstating the neural signal transmission.

Neuromodulation technology for treatment of movement and neuropsychiatric disorders may provide therapeutic benefits by directly disrupting brain activity. Deep brain stimulation works by sending synchronous, fixed-interval trains of electrical stimulation pulses from a small number of channels to modulate the brain activity. Some other neurodegenerative diseases such as Alzheimer's or stroke, for example, cannot be treated with deep brain stimulation-based interventions. Rather a closed-loop system may be used to bypass a damaged, diseased, or damaged and diseased brain region by reinstating the region's input/output properties to restore cognitive functions. Accordingly, a cortical prosthesis may use real-time delivery of precise large-scale spatiotemporal patterns of asynchronous electrical pulses to mimic the neural code.

Some implantable neurostimulators may require pre-defined user inputs of pulse patterns and timing. A closed-loop deep brain stimulation may send pre-loaded stimulus pulses when sensing abnormal neural activity. For example, one neuromodulation implant for small animal experiments contains a four channel neurostimulator to deliver user-defined stimulation pulses. An example system-on-chip design includes 160-channel stimulation, and 16-channel recording for use in spinal cord stimulation.

In an example, a closed-loop processing unit from a same electrode may allow for real time adjustment of stimulation pulses in response to variations in neural response as may be needed by a cortical prosthesis. For example, neuroinflammation caused by intracortical implantation may weaken a neuron-electrode interface by encapsulating glial cells (a supportive cell in the central nervous system) around the implant. Monitoring the effect of stimulation of a region while the region is being stimulated, e.g., simultaneously or near simultaneously, may enable validation and optimization of the stimulus for safe and precise charge delivery over time.

Hippocampal memory prosthesis is a form of neural prosthesis that aims to restore cognitive functions lost in injures or diseases due to destruction of neurons and their connections in a specific region of the brain. Hippocampal memory prosthesis may rely on a computational model that mimics the nonlinear dynamical multi-input, multi-output (MIMO) properties of the neural circuit to be replaced. The MIMO model may enable the prosthesis to stimulate a downstream brain region with appropriate output spatiotemporal patterns of neural codes predicted from input spatiotemporal patterns of neural activities recorded from an upstream brain region. By reinstating the neural code processing and transmission, the damaged brain region may be bypassed, and the cognitive function may be thus restored. To implement a hippocampal memory prosthesis, it may be necessary to be able to deliver temporally and spatially distributed neural code-based stimulation patterns to the brain tissue with multiple electrodes.

Existing neural interface technologies for brain implantation, as in DBS, utilize fixed interval trains of pulses, with a single or small number of stimulation electrodes. However, to enable neural code-based stimulation, as may be needed by the hippocampal memory prosthesis, a system for real-time precise delivery of large-scale spatiotemporal patterns of electrical pulses may be designed and implemented. In addition, the ability to stimulate and record from the same electrode may be needed for mimicking the neural code. This capability may maximize the number of electrodes for recording or stimulation, provide feedback from stimulated tissue for validating stimulation effects and optimizing stimulation parameters, and may enable the building of a single neuron-level MIMO model. The features may also be desirable in applications such as the closed-loop DBS for treatment of neurological disorders. For example, multi-channel DBS may provide more focal and effective modulations to the brain compared with single-channel DBS. DBS parameters such as the pulse width, waveform, frequency, amplitude and duration can be more effectively tuned based on feedback from neural activities. Accordingly, a configurable multi-channel neurostimulator with feedback recording capability may potentially enable safer, more precise, and efficient DBS treatments.

A challenge of generating large-scale stimulation pulses is hardware efficiency. Power and area may be important parameters of an implantable solution. A solution of separate pulse generators for each electrode is inefficient for a hippocampal memory prosthesis. This is because the natural rate of neural activity is slow, so each pulse generator would need to spend an amount of time in quiescent mode, which still may consume power. Whereas, time multiplexing a single pulse generator into multiple channels may enable combining several current sources into a single high rate pulse generator. Furthermore, neural spiking activity may be sparse in nature and simultaneous pulse generation from multiple electrodes will not result in sparse neural code. On the other hand, asynchronous low magnitude stimulation pulsing has the potential of generating sparse neural code. Accordingly, a highly configurable and asynchronous neurostimulator may enable an assessment of whether sparse low amplitude pulses would generate sparse neural code.

A challenge of recording in conjunction with stimulation may be due to the prolonged saturation of the recording amplifier caused by stimulus artifacts, which may mask neural activities of interest. Stimulus artifacts may last for tens of milliseconds or even hundreds of milliseconds depending on the amplifier, electrode property, tissue property, and stimulus parameters. Minimizing such recording contaminants may be necessary for better recording of evoked neural activities and controlling neural interface devices.

In an example embodiment, a highly configurable asynchronous multi-channel neurostimulator that can be driven by a MIMO model-based computational unit to continuously generate neural code-like spatiotemporal patterns of stimulation pulses with adjustable pulse parameters is proposed. Stimulation pulses may be generated in real-time driven by an external source (e.g., the output of the MIMO model) and feedback from the neural response to stimulation from the stimulated tissue may be used in the generation of the stimulation pulses. Each stimulation channel may be equipped with a switching mechanism designed to reduce the recovery period from an artifact from tens to hundreds of milliseconds to ~2 ms. The system has been designed, fabricated and characterized first in simulations (or phantoms) and then in the hippocampi of behaving rats. In vivo recordings demonstrate recovery of early onset compound potentials. In an example embodiment, recording of spike activity may also be possible with this system based on results from simulated or phantom recordings.

The geometric area of the electrode may limit recording of spikes. Accordingly, in some example embodiments, because the same electrode may be used for stimulation and recording, the surface area of the electrode may need to be large to allow for a charge storage capacity that allows delivering enough charge to the tissue to evoke a response.

FIG. 1. is a diagram illustrating a representation of a brain 100 having a cognitive prosthesis device 102 implanted. The device 102 may communicate with the brain 100 through multielectrode arrays 104 to bypass a damaged region 106. In an example, one task may be to design a system that allows recording in conjunction with stimulation. Recording in conjunction with stimulation may be difficult because of prolonged saturating stimulus artifacts which may mask neural activity that may be of interest. Artifacts may last for milliseconds or possibly tens of milliseconds depending on the acquisition device, electrode property, tissue property, and stimulus parameters. The elimination of such saturating stimulus artifacts may be needed for better understanding of stimulus induced neural activity and control of the cognitive prosthesis 102.

Techniques used for stimulus artifact rejection may include, but are not limited to, subtraction techniques and blanking techniques. Subtraction techniques may subtract a signal matching the stimulus artifact from contaminated neural data. The subtraction techniques may be coupled with digital signal processing algorithms such as finite impulse response (FIR) filtering and infinite impulse response (IIR) temporal filtering. However, subtraction techniques may not fully eliminate artifacts because generation of an accurate template, e.g., a signal matching the stimulus artifact from contaminated neural data, may require that the overall shape and dynamic range of the artifact does not change. The template may be difficult or impossible to match to a signal that changes overall shape and dynamic range.

Blanking techniques may include shutting off or disconnecting a neural recording system during stimulation. The blanking techniques may be implemented for stimulus artifact rejection from neighboring electrodes, but in an example, blanking techniques may not be implemented for stimulus artifact rejection for the same electrode. The blanking techniques may not be implemented for the same electrode because residual charge on the electrode after stimulation due to a slight mismatch in the biphasic pulse may contaminate the amplifier after the blanking period.

An example embodiment may include a highly configurable multichannel stimulator which may be triggered by a "brain-like" computation unit to generate continuously any arbitrary spatiotemporal patterns of stimulation pulses in real time. "Brain-like" may include systems that mimic the generation of brain pulses, e.g., any arbitrary spatiotemporal patterns of stimulation pulses in real time. Stimulation may be synchronized with a set of serially controlled switches, e.g., Complementary Metal-Oxide-Semiconductor (CMOS) switches to completely block out the stimulus from the recording amplifier during stimulation. Charge balance may be achieved by using biphasic pulses and shorting the electrode to ground after each pulse before recording is resumed. An example design may include a stimulation pattern generator, a controller (e.g., one or more microprocessors, microcontrollers, central processing units, digital logic, or any other circuitry that may implement a controller), a multiplexer and a set of serially controlled switches, (e.g., CMOS switches) for stimulus artifact rejection.

Figure 2:
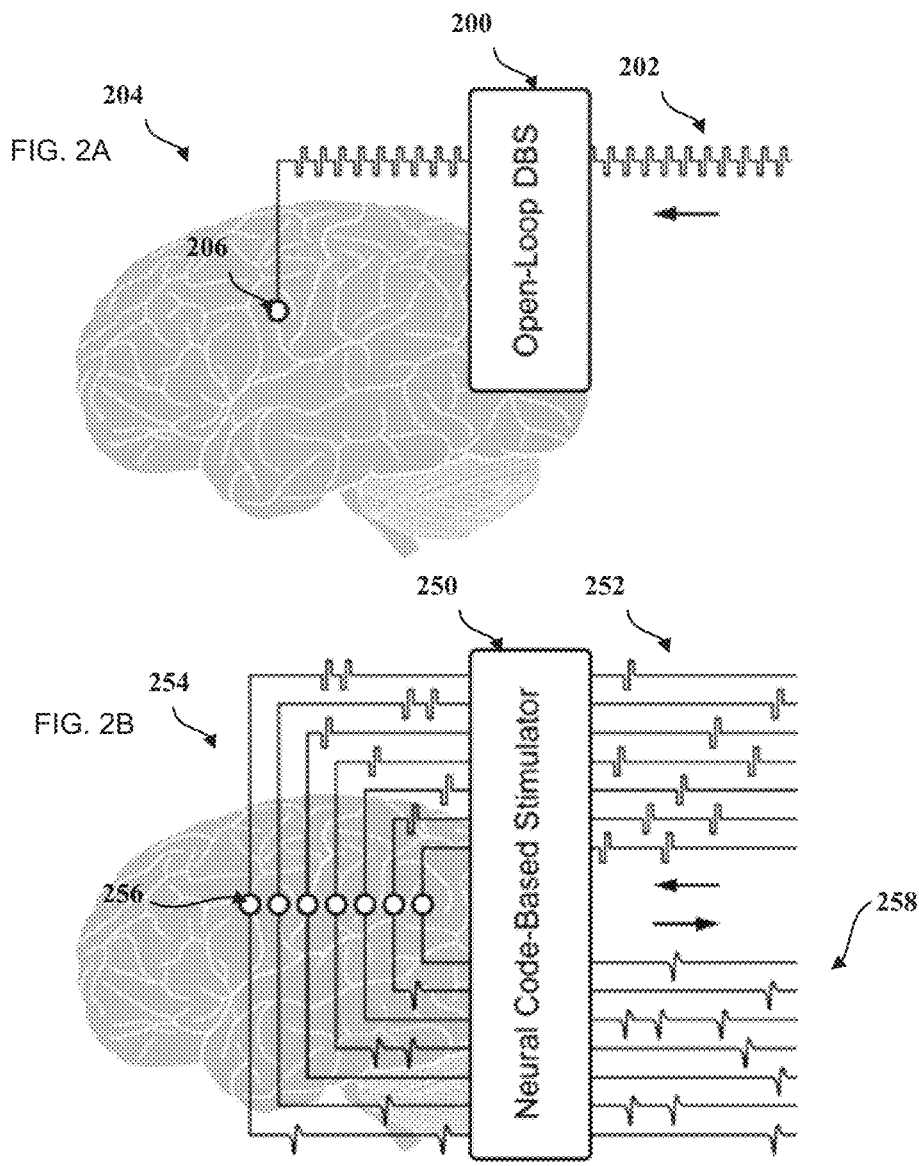
FIG. 2A is a diagram illustrating an open-loop deep brain stimulation using an open loop DBS.
FIG. 2B is a diagram illustrating a configurable multi-channel neurostimulator 250 with stimulus artifact suppression for implementing closed-loop processing from the region of stimulation.

FIG. 2A is a diagram illustrating an open-loop deep brain stimulation using an open loop DBS 200. As illustrated in FIG. 2A, a single signal 202 may be generated. The single signal 202 may be input into the brain 204 on a single electrode 206 to stimulate the brain 204. With open-loop deep brain stimulation 200, feedback from the stimulation is not considered in the generation of the signal 202, i.e., the device (open-loop DBS 200) functions in an open loop without feedback rather than a closed loop with feedback.

FIG. 2B is a diagram illustrating a configurable multi-channel neurostimulator 250 with stimulus artifact suppression for implementing closed-loop processing from the region of stimulation. As illustrated in FIG. 2B, multiple signals 252 may be generated. The signals may be input into the brain 254 on multiple electrodes 256 to stimulate the brain 254. With configurable multi-channel neurostimulator 250, feedback 258 from the stimulation may be considered in the generation of the signals 252, i.e., the device (configurable multi-channel neurostimulator 250) functions in a closed loop with feedback rather than in an open loop without feedback.

Figure 3:
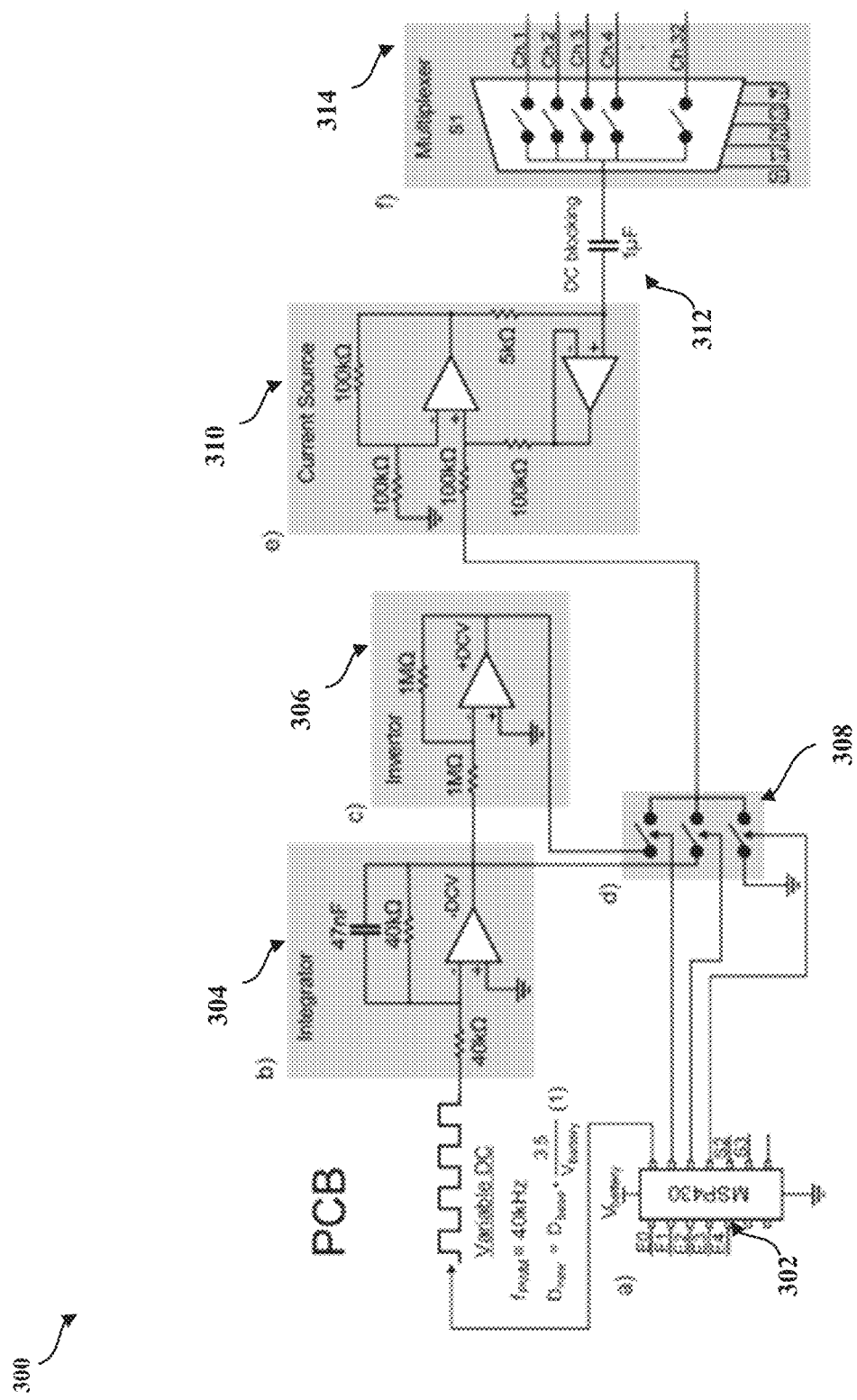
FIG. 3 is an example design of a 32-channel configurable constant current biphasic neurostimulator 300.

FIG. 3 is an example design of a 32-channel configurable constant current biphasic neurostimulator 300. Example embodiments may include a stimulation pattern generator (e.g., within a microcontroller 302), a multiplexer 314, a micro-processor-based controller (microcontroller 302), and a set of serially controlled CMOS switches 308 for stimulus artifact suppression (SAS). For example, the design 300 includes the microcontroller 302. In the illustrated example of FIG. 3, the microcontroller 302 is an MSP430. In other examples, other microcontrollers, microprocessors, circuitry, configurable logic, or other devices or combinations of devices may be used in place of or in addition to the MSP430 microcontroller.

The microcontroller 302 may generate a pulse width modulation (PWM) signal, e.g., at 40 kHz. The PWM signal may have an adjustable duty cycle to configure the stimulus amplitude. The duty cycle may also automatically adjust as a battery supply voltage drops, e.g., the battery supply voltage powering the circuitry. In an example, the automatic adjustment of the duty cycle may be governed by EQ. 1A. Automatic adjustment of the duty cycle may avoid the need for a voltage regulator.

$$D_{new} = D_{base} * \frac{3.5}{V_{battery}}, \quad \text{(EQ. 1A)}$$

where $D_{new}$ is the adjusted duty cycle; $D_{base}$ is the target duty cycle for when the battery voltage is 3.5V, and $V_{battery}$ is the voltage of the battery at a time point.

The PWM signal may be input to an integrator 304 to generate a constant negative DC voltage (−DCV). The constant negative DC voltage (−DCV) may be an input to an analog inverter circuit 306 to generate a positive DC voltage (+DCV). A set of analog switches 308 may set the polarity and duration of the pulse controlled by the microcontroller 302. For example, the set of analog switches 308 may select between the −DCV and +DCV signals to set the polarity. The analog switches and/or the microcontroller 302 may set the duration of the pulse. The switches may be controlled by the microcontroller 302. A voltage to current converter 310 and a DC blocking capacitor 312 may generate safe single channel constant current biphasic pulses. As illustrated in FIG. 3, a multiplexer 314 may be used to expand the design to, e.g., 32 channels or some other number of channels.

In another example circuit, the stimulator may include a configurable constant current biphasic and monopolar waveform generator and a pattern generator independently specifying spatiotemporal timings and magnitudes of pulses across 32 stimulating electrodes. First, a single-channel configurable current source capable of providing charge-balanced biphasic pulses may be designed and tested as follows. A low-power microcontroller (MSP430G2553, Texas Instrument) may be programmed to generate a 40 kHz pulse width modulator (PWM). An op-amp integrator with a cut-off frequency of 4 kHz may be designed and used to average the PWM to output a negative DC voltage, which is then inverted to output a positive DC voltage using an inverting amplifier. Three other signals from the microcontroller may be generated to drive analog switches (e.g., TS5A22362) dictating polarity and duration of each pulse or the inter-pulse intervals. An op-amp-based current source may be designed to convert the output voltage biphasic pulses to constant current biphasic pulses with a 1 μA resolution. The output of the current pulse may be fed into a multiplexer to expand a single channel to 32 channels. A DC blocking capacitor may be placed at the input of the multiplexer to block input off-set. Since the application of the design may only need a sparse and low pulse rate, charge build-up may not be expected as the electrode may be shorted to ground after each stimulation pulse.

The example circuit may be powered by two 3.7V coin batteries connected in series to obtain ±3.7V. The absolute maximum supply rating may be determined by the microcontroller, which may be +4.1V. Other chips have a maximum voltage rating of ±5V. To minimize hardware design for future miniaturization of the PCB, voltage regulators are eliminated since all chips can operate at a minimum voltage of ±3V. To ensure the output DC voltage from the PWM stays constant even with voltage supply drop, the microcontroller may be programmed to sample the supply voltage and adjust the PWM duty cycle according to EQ. 1B, which is adjusted from EQ. 1A to account for the battery voltage of 3.7 volts:

$$D_{new} = D_{base} * \left(\frac{3.7}{V_{battery}}\right), \quad \text{(EQ. 1B)}$$

where $D_{new}$ is the adjusted duty cycle; $D_{base}$ is the target duty cycle for when the battery voltage is 3.7V, and $V_{battery}$ is the voltage of the battery at a time point.

Figure 4:
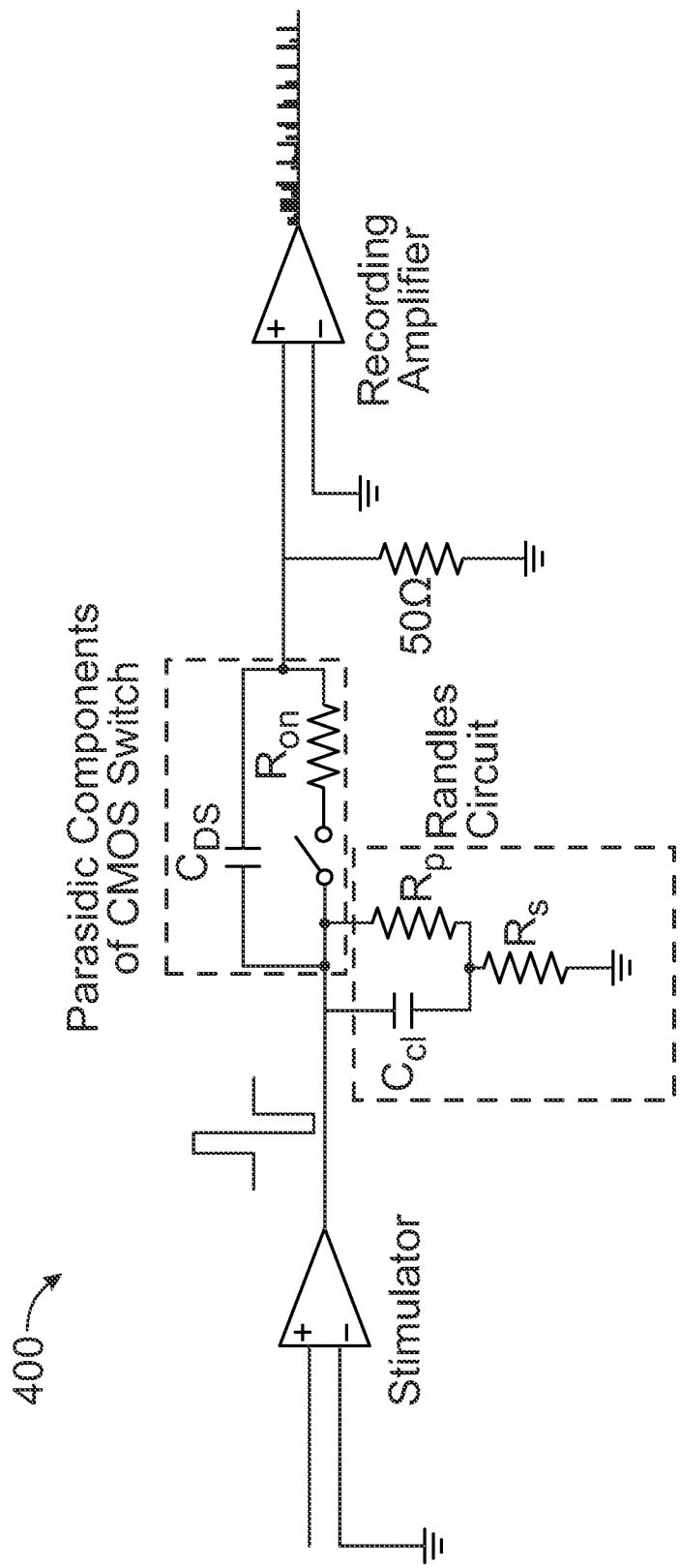
FIG. 4 is a diagram illustrating sources of error when using the switching technique to block stimulus artifacts, which may include (a) polarization voltage on the electrode due to faradaic reactions or charge imbalance, and (b) parasitic capacitance across the source and drain of the switch.

FIG. 4 is a diagram illustrating sources of error when using the switching technique to block stimulus artifacts, which may include (a) polarization voltage on the electrode due to faradaic reactions or charge imbalance, and (b) parasitic capacitance across the source and drain of the switch. Another issue is that CMOS analog switches may contain parasitic components that may affect the alternating current performance of the device. A parasitic capacitor across the source and drain of each switch may couple part of the stimulus signal into the input of the amplifier when the switch is open. To attenuate the effect of this error source, a small resistor of, e.g., 50Ω, may be connected between the input of the amplifier and ground, effectively creating a voltage divider with the input at the source and output at the drain of the switch for when the switch is in an open state. The voltage divider technique demonstrated effective attenuation of the artifact due to parasitic capacitor in the analog switch down to input referred noise level of the amplifier at 10 μV. While the small resistor is indicated to be 50Ω, it will be understood that a wide variety of resistor values may be used depending on the voltages involved, the specifications of the CMOS switches used, such as resistance, capacitance, inductance, and other specifications of the CMOS switches used in a particular implementation.

Figure 5:
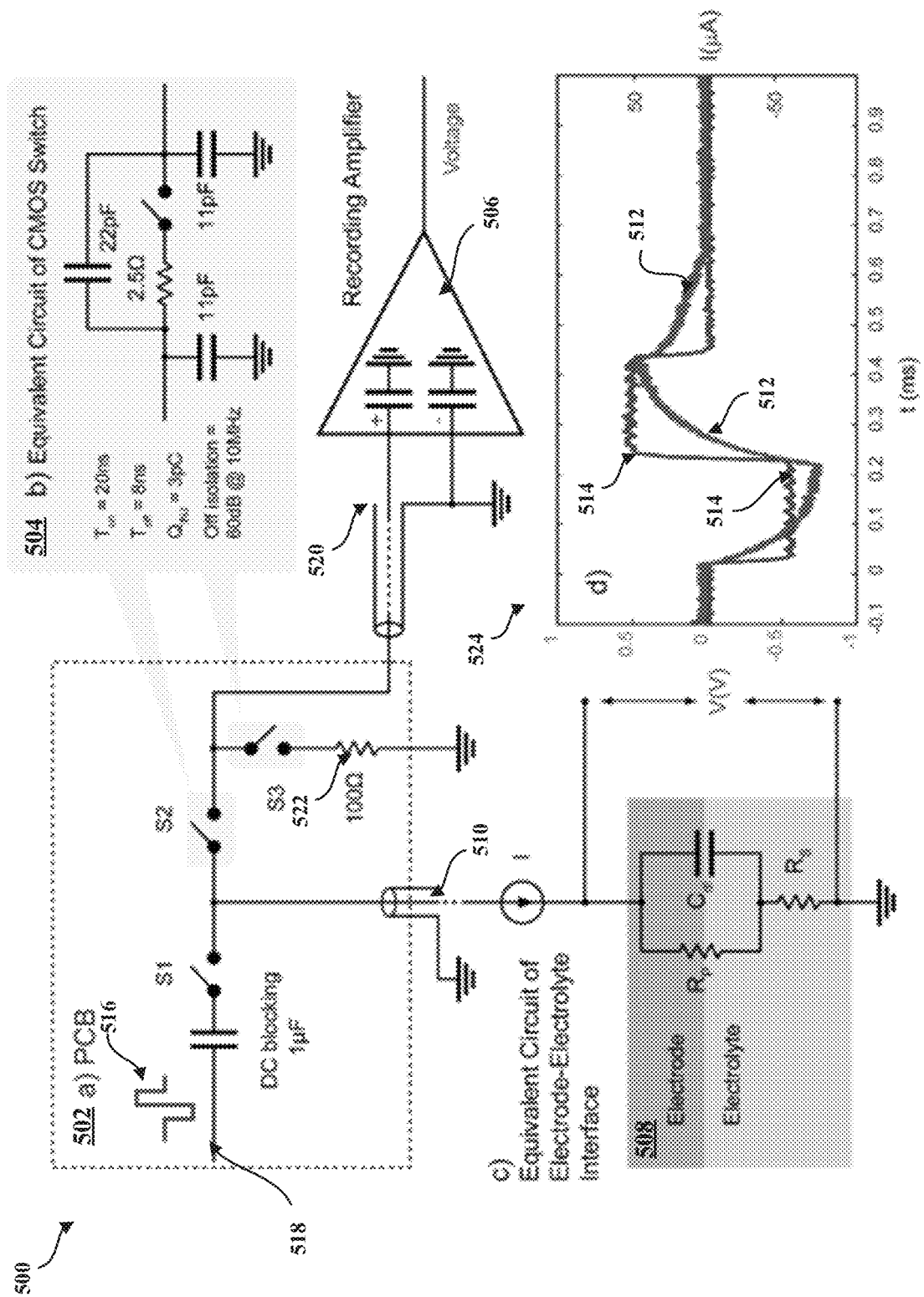
FIG. 5 is a diagram illustrating a stimulation artifact suppression set-up 500.

FIG. 5 is a diagram illustrating a stimulation artifact suppression set-up 500. The stimulation artifact suppression set-up 500 may synchronize the stimulation 516 at input 518 with a set of serially controlled CMOS switches (S2) on a PCB 502 to block out the stimulus 516 from the recording amplifier 506 during stimulation while connecting the amplifier input 520 to a resistor 522, e.g., 100Ω, via a switch (S3). Connecting the amplifier input 520 to a resistor 522 via a switch (S3) may prevent ringing that may be caused in the recording system due to any extra charge coupled across the switch (S2). Charge coupling across the switch (S2) may be due to parasitic capacitance of the switch (S2).

An example model switch 504 illustrates parasitic capacitance components of analog switches such as S2 and S3. The parasitic components of the analog switches (S2, S3) at 504 may include parasitic capacitors, as illustrated at 504. The PCB 502 may be connected to the recording amplifier 506 and the electrode 508 using a coaxial cable 510. The timing of the switches in the PCB 502 may be determined based on the electrochemical properties of the electrode 508. The voltage transient across a microelectrode illustrated at 512 may be in response to a biphasic cathodic first current pulse 514. In the example of FIG. 5, $R_S$ represents the electrolyte resistance, $R_P$—represents faradaic reaction, and $C_{d1}$ represents capacitive reactions at the interface.

Neural recording systems may include small-signal voltage amplifiers, e.g., 10 μV-10 mV, to provide adjustable gain amplifiers and bandpass filters. Amplification to voltage levels beyond the power supply voltage of an amplifier cannot be produced by the amplifier. A large signal may be defined as an amplifier input signal having a voltage that may result in an amplified output signal having a voltage above a supply voltage. Not only may a large signal cause signal distortion and loss of a neural signal, the excess power transfer may damage the amplifier over time. A stimulation pulse applied to an electrode may be a large signal. When a stimulation pulse is used in conjunction with a neural recording system, the stimulation pulse may produce high amplitude artifacts with long recovery periods caused by amplifier saturation and filter ringing.

To prevent a blockade of neural data by a stimulus artifact, CMOS switches (e.g., ADG714 is one example) may be used to block the stimulation current from transmitting to the recording system. Each switch may be connected between the electrode and the recording system and may be synchronized with the stimulator to be triggered a short time before and after the stimulation pulse. During this time, the switches connecting the electrodes to the recording module (S2) will be kept open and the switches connecting the stimulator to the same electrodes (S1) will be closed (see PCB 502).

When using CMOS analog switches to block the stimulus from the recording system, it may be necessary to deal with parasitic components within the CMOS switch that affect the AC performance of the device as illustrated at 504. This means that part of the stimulus may couple from the source to the drain of S2 during stimulation. S2 acts to minimize charge coupling into the amplifier but since the amplifier is typically set to a gain of at least 60 dB, even small voltages may generate long contaminated signals.

To dissipate the charge coupled across the switch during stimulation, a 100Ω resistor 522 may be used at the input of the amplifier 406 during stimulation to suppress ringing. (As discussed above, other resistor values may be used.) The resistor 522 may also be used to absorb any instantaneous charge coupled from the electrode 508 to the amplifier 506 when the electrode 508 is reconnected to the amplifier 506. The resistor 522 is disconnected from the amplifier when recording is resumed using another CMOS switch (S3) (PCB 502). The timing of the switches may depend on the shape of the voltage transient waveform across the electrode in response to a given stimulation pulse and is determined by the electrochemical properties of the interface as described below.

The shape of the voltage transient across a microelectrode may be a factor of the electrochemical processes at the interface which may be estimated with an electrical equivalent circuit model. The model may include an electrolyte resistance ($R_S$) in series with the parallel combination of a double layer capacitance ($C_{d1}$) and an impedance of faradaic reactions ($R_P$) (illustrated at FIG. 3, electrode 508). Equation 2 (EQ2) describes an example relationship between an applied constant current pulse (I) and the resulting voltage (V) across the interface:

$$V(t) = IR_s + IR_p\left(1 - e^{\frac{t}{R_P C_{d1}}}\right) \quad (EQ. 2)$$

An example of the voltage transient in response to a stimulation current pulse of 60 μA, 200 μs is illustrated in FIG. 3 at waveforms 524. With the example model, capacitive charge injection represented by $C_{d1}$ may involve physical absorption and desorption of ions in an electrolyte. The Faradaic reaction represented by $R_P$ may involve the local donation of electrons through oxidation and reduction reactions, which may be less desirable than a capacitive process because the local donation of electrons through oxidation and reduction reactions may involve the formation of new species. Both charge injection mechanisms may be involved during stimulation (irreversible faradaic reactions are to be avoided). Thus, the time constant of the electrode may be governed by equation 3 (EQ 3):

$$\tau = R_p * C_{d1} \quad (EQ.3)$$

Figure 6:
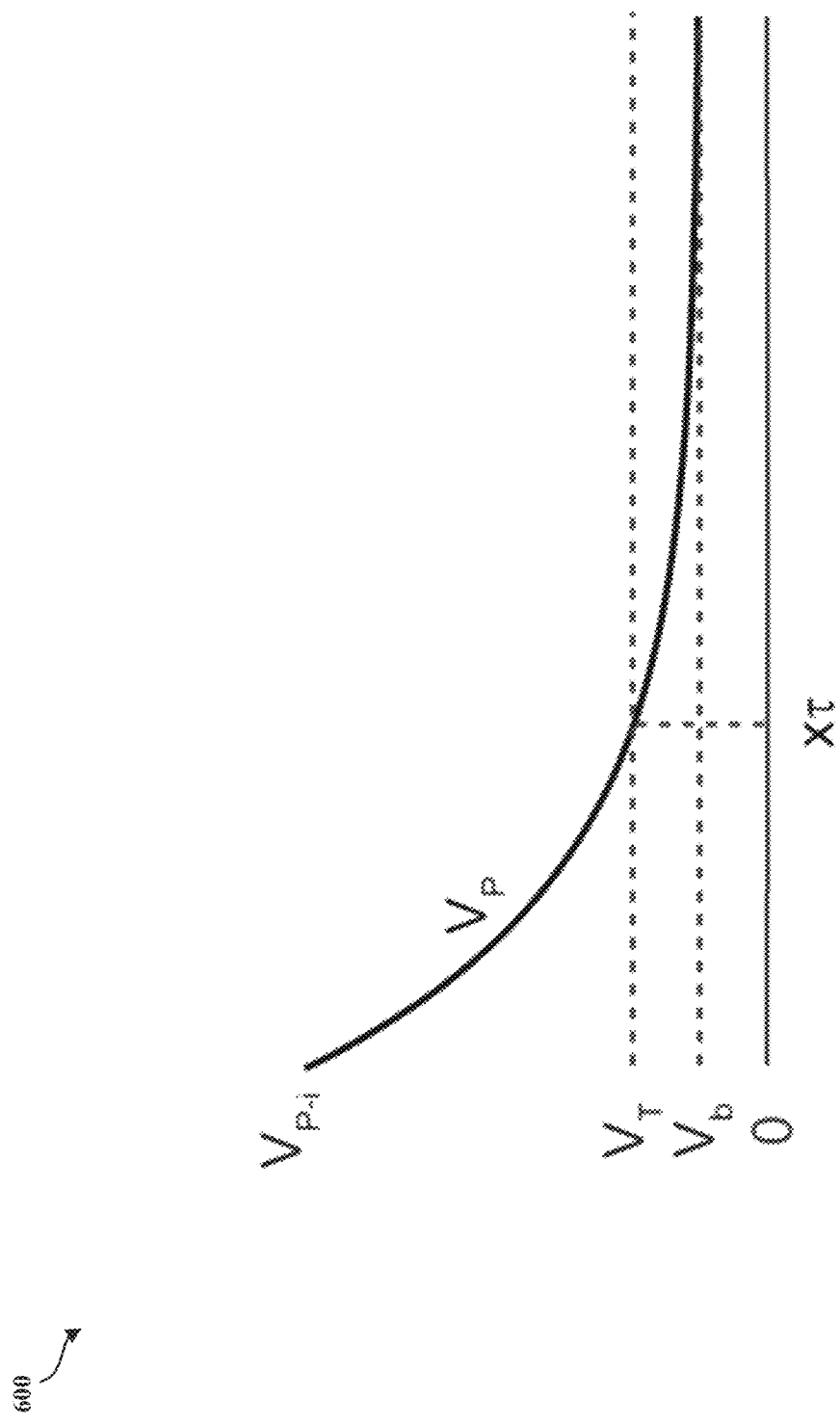
FIG. 6 is an example polarization voltage (VP) across the electrode with respect to a reference of the same material after termination of the stimulation pulse with an initial value of $V_{P\text{-}i}$.

FIG. 6 is an example polarization voltage ($V_P$) across the electrode with respect to a reference of the same material after termination of the stimulation pulse with an initial value of $V_{P-i}$. The voltage may drop below $V_T$ before recording is resumed, to avoid amplifier saturation, which takes a time duration of multiple factors of τ represented as xτ. For example, after the termination of the stimulation pulse, the electrode may be left with an initial polarization voltage ($V_{p-i}$) and may take several time constants (xτ's) to reach to a value close to its initial bias level ($V_b$) (FIG. 6). $V_{p-i}$ is defined as:

$$V_{p-i} = V_b + (\Delta V - V_a) \quad (EQ. 4)$$

where $V_a$ is the instantaneous voltage drop after the termination of the current pulse and ΔV is the maximum voltage the electrode reaches at the end of the pulse. $V_b$ is generally a few millivolts with respect to a large return electrode of the same material, as is the case of electrophysiology experiments. It is often difficult to identify $V_a$ in a voltage transient plot, thus $V_{p\_i}$ cannot be accurately determined in some cases. Alternatively, $V_{P\_max}$, the maximum polarization voltage across an electrode to avoid potential exertion beyond the water window, may be used as $V_{p-i}$. This is a worst-case scenario. This value is experimentally determined and is electrode material dependent.

It may be important that the polarization voltage on the working electrode ($V_p$) with respect to a reference of the same material, drops to below a threshold before recording is resumed to avoid saturation of the amplifier. This threshold may be governed by the settings on the recording amplifier such that:

$$V_p < \frac{V_{max-amp}}{\text{Gain}} = V_T \qquad \text{(EQ. 6)}$$

where $V_{max-amp}$ is the maximum output voltage from the recording amplifier, and Gain is the gain of the amplifier.

Figure 7:
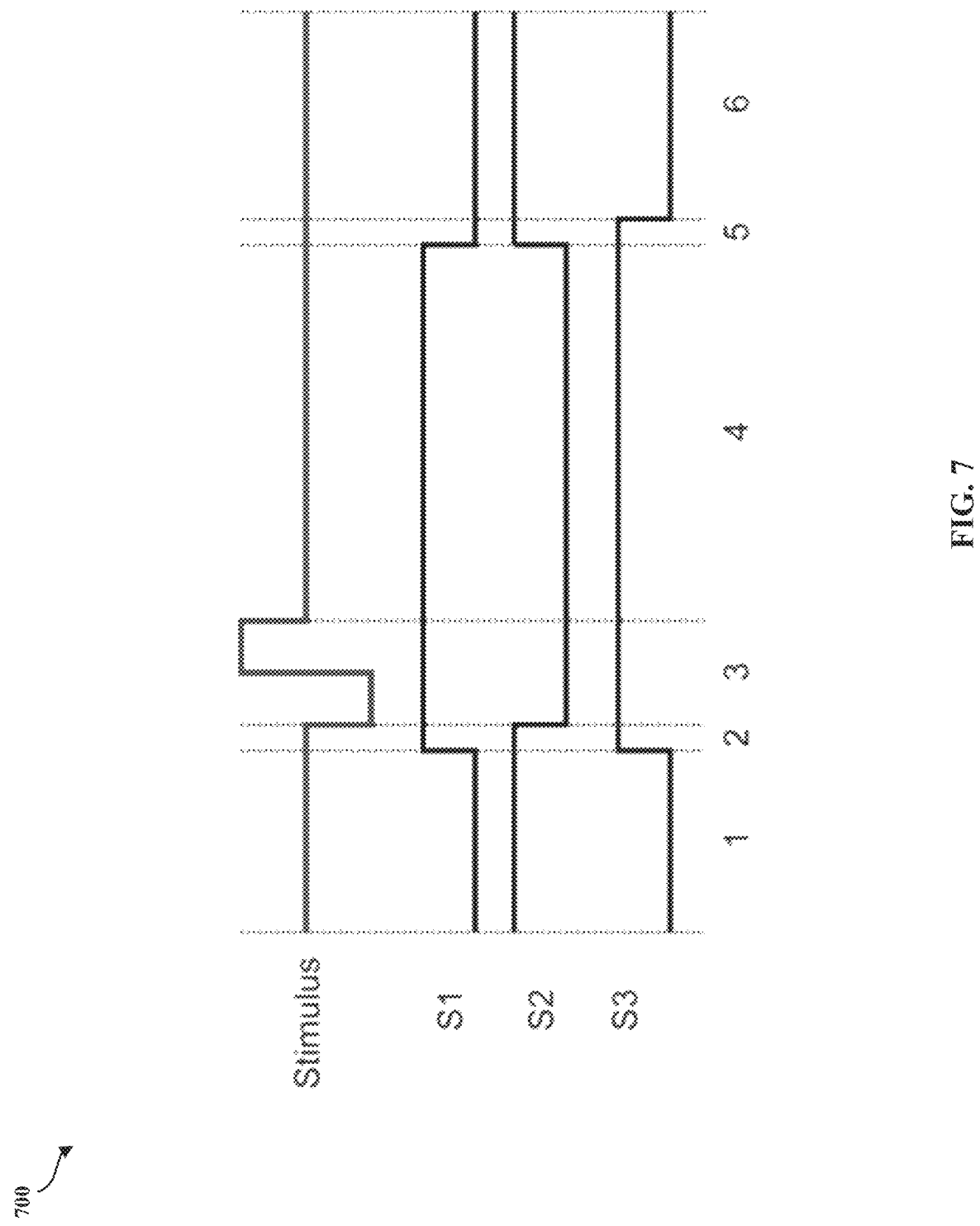
FIG. 7 is a diagram illustrating the state of the switches S1, S2, S3 of FIG. 5.

FIG. 7 is a diagram illustrating the state of the switches S1, S2, S3, of FIG. 5, PCB 402. In FIG. 7, "1" (one) is an indication that a switch is closed and "0" (zero) is an indication that a switch is open. FIG. 7 illustrates an example of the state of the switches S1, S2, S3 with respect to a stimulation pulse 516 into the input of the PCB 502. In the illustrated example embodiment, when the input 518 to the PCB 502 is not pulsing, the input 518 to the PCB 502 is connected to ground.

After the termination of the stimulation pulse, the electrode may take several time constants (xτ) to approach to below $V_T$, which may dictate the time duration the electrode may need to stay disconnected from the amplifier. The timing and state of the switches are illustrated in FIG. 7. States 1 to 6 are as follows:

State 1 is recording. The stimulus=0 volts, S1=0 (open), S2=1 (closed), and S3=0 (open). With S2 closed, the electrode 508 is connected to the recording amplifier 506 while the stimulator, e.g., at input 518, and the resistor 522 are disconnected. The stimulator and the resistor at the input of the amplifier are disconnected while the electrode is connected to the amplifier. This is the recording phase.

In state 2, Grounding, stimulus=0 volts, S1=1 (closed), S2=1 (closed), and S3=1 (closed). With S1, S2, and S3 all closed, 200 µs before stimulation, the stimulator (at input 518) is connected to the electrode 508 and the resistor 522 is connected to the input 520 of the amplifier 506. For example, 200 µs before the initiation of the stimulation pulse, S1 and S3 close.

At state 3, Stimulation, stimulus occurs, S1=1 (closed), S2=0 (open), and S3=1 (closed). Accordingly, the amplifier 506 is disconnected from the electrode 508. The stimulation pulse is then applied to the electrode 508. For example, S2 then opens to disconnect the recording system and the stimulation pulse is applied to the electrode.

At state 4, Discharge period, stimulus=0 volts, S1=1 (closed), S2=0 (open), and S3=1 (closed). The electrode 508 stays disconnected from the amplifier 506 until the polarization voltage on the electrode 508 falls below $V_T$. For example, the switches stay in that state for the duration of the pulse plus a predefined xτ.

At state 5, Discharge of residual charge (200 µs), stimulus=0 volts, S1=0 (open), S2=1 (closed), and S3=1 (closed). Accordingly, the electrode 508 is disconnected from the stimulator and connected to the recording system. The resistor 522 remains connected to the input 520 of the amplifier 506 to absorb any charge injection due to residual offset on the electrode 508. For example, S1 then disconnects the electrode from the stimulator and S2 reconnects the electrode to the amplifier while the input of the amplifier is still connected to ground through the 100Ω resistor to absorb any instantaneous charge injected from the electrode.

At state 6, Recording resumed, stimulus=0 volts, S1=0 (open), S2=1 (closed), and S3=0 (open). Accordingly, the termination resistor 522 is disconnected, and recording is resumed. For example, 200 µs later, the resistor is then disconnected by S3 and recording is resumed.

The electrochemical properties of an electrode may be characterized for different media to determine different time constants of the electrode-electrolyte. Factors that affect the value of the time constant include electrode material, geometric and effective area of exposed region, and the electrolyte impedance. Thus, an electrode should be separately characterized for in vivo or in vitro experiments.

Figure 8:
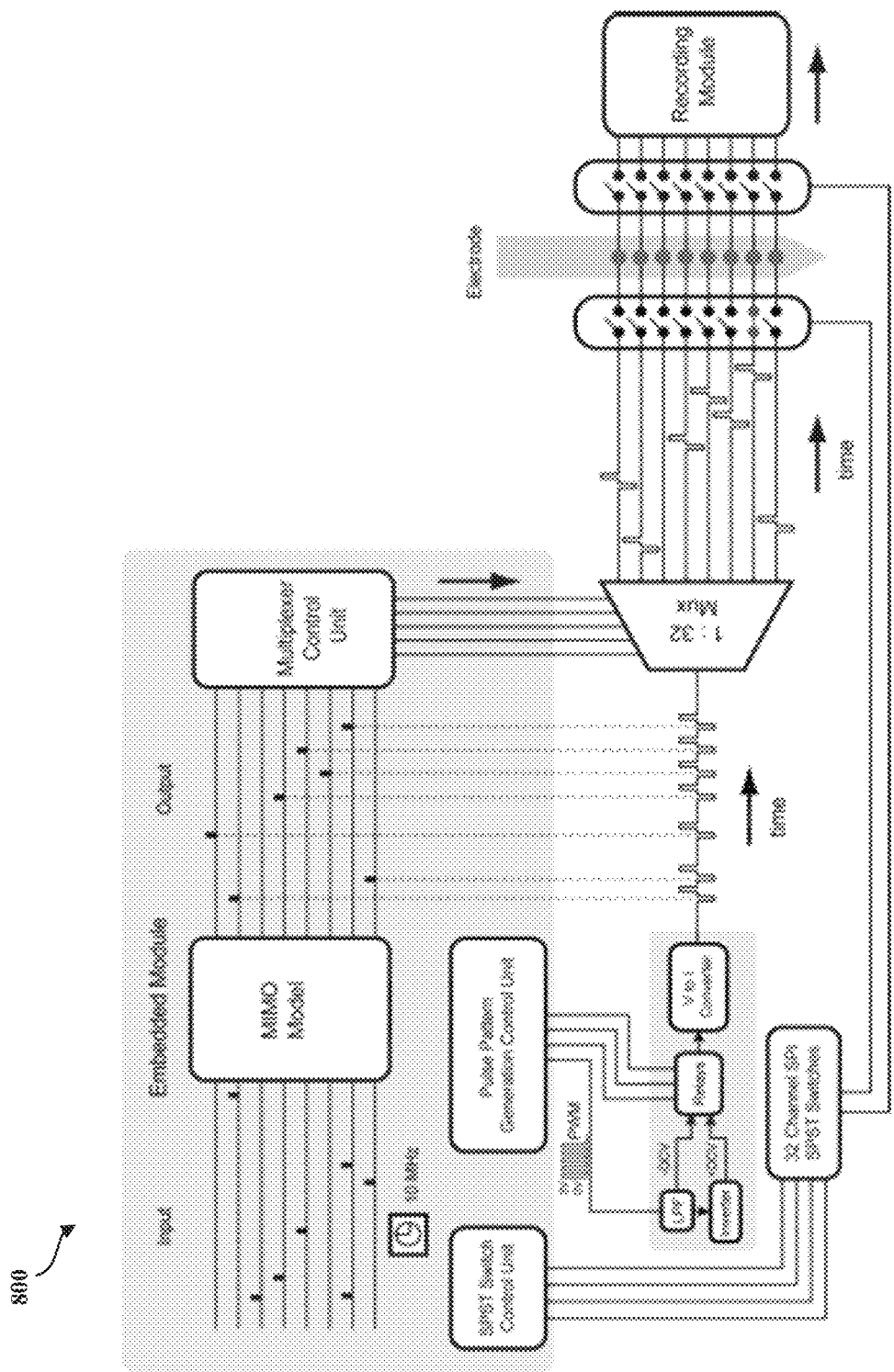
FIG. 8 is a block diagram illustrating a closed-loop multi-channel stimulator and corresponding data flow of the closed-loop multi-channel stimulator.

FIG. 8 is a block diagram illustrating a closed-loop multi-channel stimulator 800 and corresponding data flow of the closed-loop multi-channel stimulator 800. FIG. 8 illustrates and example stimulation pattern generator circuit design for the closed-loop multi-channel stimulator 800.

The stimulator 800 includes a configurable constant current biphasic and monopolar waveform generator and a pattern generator specifying a spatiotemporal pattern across 32 stimulating electrodes. A single channel configurable current source capable of providing charge balanced biphasic pulses is first designed and tested. A low power microcontroller (e.g., MSP430G2553 from Texas Instruments) may be programmed to generate a pulse width modulator (PWM) that can vary the stimulus amplitude with an accuracy of 1 µA. Using an integrator, the PWM may be averaged to output a negative DC voltage, which is then inverted to generate a positive DC voltage. Three other signals from the microcontroller were generated to drive relays dictating polarity and duration of each pulse or the inter-pulse intervals with an accuracy of 25 µs. An op-amp based current source may convert the output voltage biphasic pulses to constant current biphasic pulses.

Due to the sparse nature of neural spiking activity, simultaneous pulse generation from multiple electrodes is seldom needed. This may allow a highly efficient multiplexed design, where an output of current pulse may be fed into a multiplexer to expand a single channel to 32 independent channels with negligible sacrifice in temporal precision. The multiplexer may be controlled by 5 select lines, driven by a firmware-implemented multi-input, multi-output (MIMO) nonlinear dynamical model, which may be a mathematical algorithm replicating the input-output spike transformational properties of brain region. Multiplexing a single channel pulse generator into 32 channels allows for 150 pulses per second per channel if used at 100 µs pulse duration per phase. The output of the stimulator may be interfaced with electrodes through a zero-insertion force (ZIF) connector. This circuit may be powered by two 3V coin batteries connected in series to obtain +/−3V, or other power source, such as other battery types, DC power supplies, or other power sources.

To prevent contamination of neural data by stimulus artifacts, an inexpensive system is designed to block the stimulation signal from transmission to the recording system. This design may include a set of CMOS switches that are serially controlled via a master device, the microcontroller. The switches are connected between the electrode and the recording system and are synchronized with the stimulator to be triggered at the beginning of the pulse and when the pulse is terminated. During stimulation, 100-200 µs, the switches connecting the electrodes to the recording module will be kept open and the switches connecting the stimulator to the same electrodes will be closed. Each switch can be controlled independently but because stimulus artifacts saturates every electrode in the same medium, all the switches may be kept open during stimulation.

This implementation may be feasible for cognitive prosthesis because short pulse widths may be required for excitation of neural tissue. On the strength duration curve, rheobase is the minimum amount of charge necessary to stimulate an excitable tissue for a long pulse. Chronaxie is twice the rheobase current. Chronaxie for deep brain stimulation is estimated to be 60-150 µs. On the other hand, spike activity and local field potentials last for a duration of a few to tens of milliseconds. This means disconnecting the electrode from the recording system for the duration of the pulse does not cause a significant loss of neural data.

In the block diagram of FIG. 8, each block in the embedded system represent an algorithm to control the hardware. It includes a simulation of the Multiple Input Multiple Output (MIMO) model using a random number generator. The data is inputted to a multiplexer control unit to set the appropriate select lines of the multiplexer. The multiplexer control unit also sends commands to the switch control unit to control the timing of the switches connecting the electrodes to the stimulator and recording system. The pulse pattern generation unit programs the hardware to generate highly configurable constant current monopolar biphasic pulses.

One issue with using the same electrode for stimulation and recording is ensuring charge balance through the electrode at the end of each pulse, otherwise residual charge would leave the electrode with a polarization voltage that would contaminate the amplifier when the switch from the electrode to the amplifier is closed. An ideal charge balanced biphasic pulse ensures no net charge transfer at the electrode-electrolyte interface. However, due to imperfection of fabrication process of integrated circuits, a mismatch of current pulses can still occur and may need to be considered. The stimulator developed here prevents charge buildup by shorting the electrode to ground after each pulse to minimize or completely remove polarization voltage at the electrode electrolyte interface at the end of each biphasic pulse. A shorting phase of 100 µs is shown effective to completely remove any contaminant at the amplifier.

The block diagram and data stream of the neurostimulator with the stimulus artifact suppression technique includes a microcontroller that may run at a clock frequency of, e.g., 10 MHz, and may be programmed with 4 blocks of control units: MIMO model simulator, pulse pattern generation control unit, multiplexer control unit, and switch control unit. The MIMO model simulator block simulates inputs from an external source such as the output of the MIMO model using a random number generator (RNG), which are generated by the microcontroller through recording noise from a floating general-purpose pin. It also uses another set of random numbers to vary the magnitude of the stimulus simulating feedback from neural response to stimulation. The timing and magnitude information across 32 channels are then collapsed into a single array. In case two channels need to be stimulated simultaneously (which is a rare event), one may be delayed by the duration of the biphasic pulse. The pulse pattern generation unit then translates the information into commands controlling the single channel neurostimulator to generate biphasic pulses with varying timing and magnitude. Next, the multiplexer control unit activates proper select lines of the multiplexer to send each stimulus to the target channel.

The switch control unit, which is synchronized with the MIMO model simulator, controls timing and state of each switch used to suppress the stimulus artifact. The switches for each channel may be controlled individually, but because the stimulus artifact will contaminate all channels within the same media, the stimulation should be blocked from all recording channels.

In an example, the total power dissipation is dependent on the load current and the quiescent current. The output load current is dependent on the driving load (the electrode) and the stimulus waveform (pulse amplitude, pulse duration, and pulse rate), which is a variable defined by the user. Quiescent power consumption is the product of the current drawn by the supply (Icc) and the supply voltage (Vcc). Here, the quiescent power dissipation from all active parts except the microcontroller and multiplexer is 815 µW. The multiplexer consumes 60 µW. Thus, without multiplexing the system power consumption would be 815 µW*32=26 mW, whereas multiplexing reduces this number to 875 µW. The microcontroller power consumption is dependent on usage of general-purpose input output pins. To generate arbitrary pulse patterns in real-time through a single channel, 4 pins are required by the pulse pattern generation control unit (FIG. 6). Without multiplexing, the number of required pins would be 32*4=128 for 32 channels. Whereas, with multiplexing, this number would be reduced to 9. Thus, multiplexing greatly reduces power consumption and real-estate usage.

In an example, the microcontroller was programmed to generate random numbers dictating both the timing and amplitude of pulses across each of the 32 channels independently. The range of amplitudes ($I_{max}$) can be selected based on the user need and is limited to the supply voltage ($V_{supply}$) and the total impedance of the electrode-tissue interface ($|z|_{electrode}$).

$$I_{max} = \frac{V_{supply}}{|z|_{electrode}} \quad \text{(EQ. 6)}$$

$|z|_{electrode}$ includes the electrolyte resistance plus the polarization impedance across the electrode-electrolyte interface, which is frequency dependent. An electrochemical impedance spectroscopy (EIS) of the electrode is used to determine $|z|_{electrode}$ at a frequency equal to the inverse of the pulse duration. This frequency is a reasonable approximation for non-sinusoidal pulses.

A Tungsten microelectrode was used to evaluate the example system's capability to minimize stimulus artifact. The microelectrode was first characterized by its electrochemical properties, namely the magnitude of each element in the equivalent circuit model illustrated in FIG. 3c, its charge storage capacity and its τ using Cyclic voltammetry (CV) and EIS performed by Gamry Reference 600 potentiostat (Gamry Instruments, Warminster, Pa.). The return electrode was also made of Tungsten which was many times larger in area than the working electrode (WE).

Figure 9:
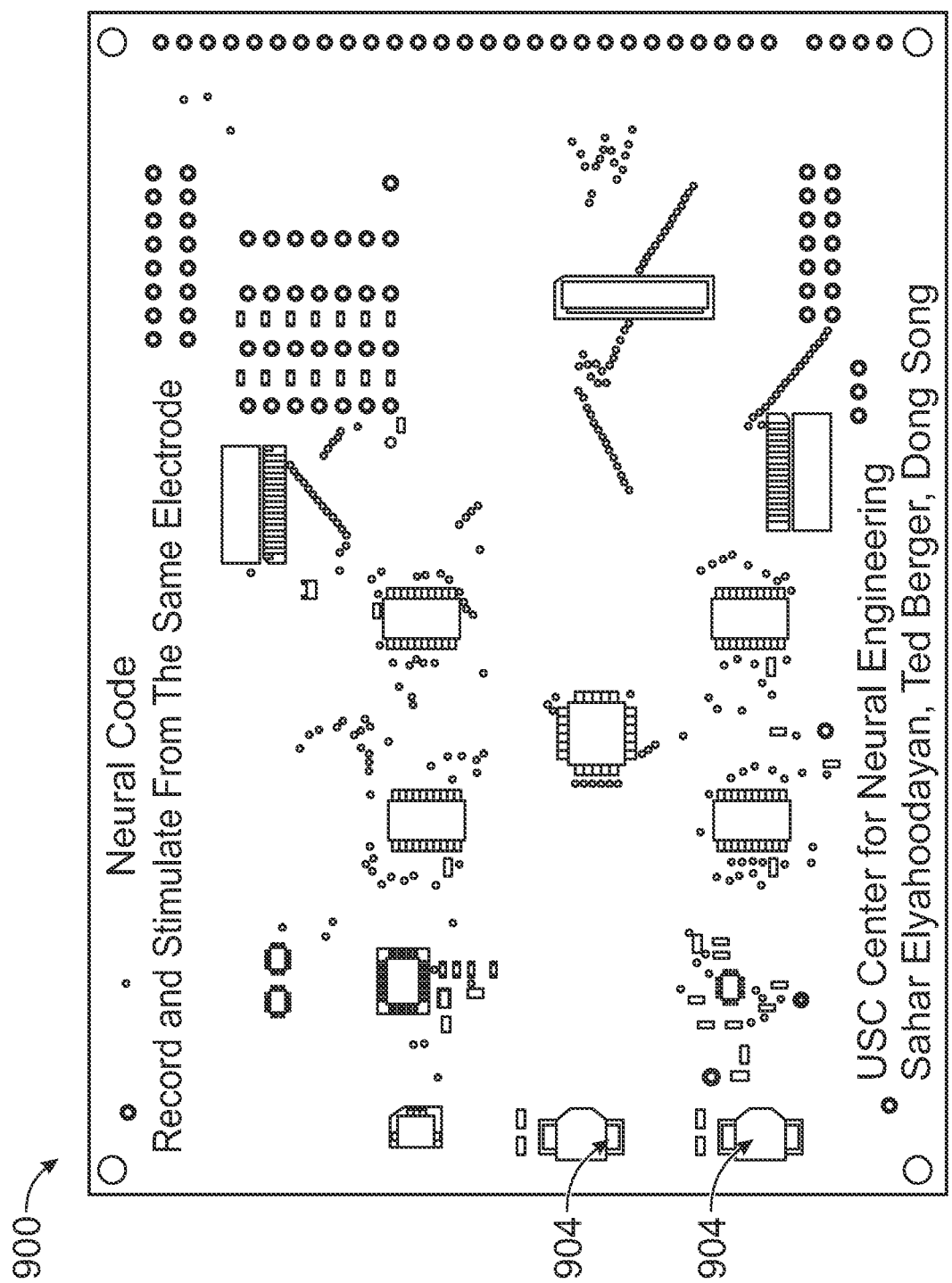
FIG. 9 is a diagram illustrating a closed-loop multi-channel stimulator PCB design.

FIG. 9 is a diagram illustrating a closed-loop multichannel stimulator PCB 900 design including a 32 channel ZIF connector, two 5 mm diameter battery holders 904, connectors, e.g., by Omnetics or other connector manufacturer, to connect to a recording system, and a ZIF connector to reprogram the microcontroller.

In an aspect, the design was tested in phosphate buffered saline with conformal coating, and more specifically, parylene C. The example design may include an electrode array organized in 4 shanks of 8 electrodes per shank. Each electrode may have a geometric surface area of ~707 µm². In an example, the platinum electrode sites were electroplated with iridium oxide to increase charge storage capacity to ~5 mC/cm² making the electrodes suitable for both stimulation and recording. A Platinum electrode was used as the return electrode which was many times larger than the stimulation electrode.

Figure 10:
FIG. 10 is a diagram illustrating a voltage transient 1000 of an electroplated 30μm diameter electrode in response to a biphasic cathodic first 100 μA, 100 μs current pulse.

FIG. 10 is a diagram illustrating a voltage transient 1000 of an electroplated 30 µm diameter electrode in response to a biphasic cathodic first 100 µA, 100 µs current pulse. The stimulus parameter used in the example may be equal to 10 nC phase-1 which is well below the charge storage capacitance of the electrodes at ~35 nC. The shape of the waveform further suggests charge injection through capacitive rather than faradaic reactions which is apparent from the linear increase of polarization voltage across the electrode-electrolyte interface. Capacitive reactions are described to be more desirable because no chemical species are consumed or created.

Figure 11:
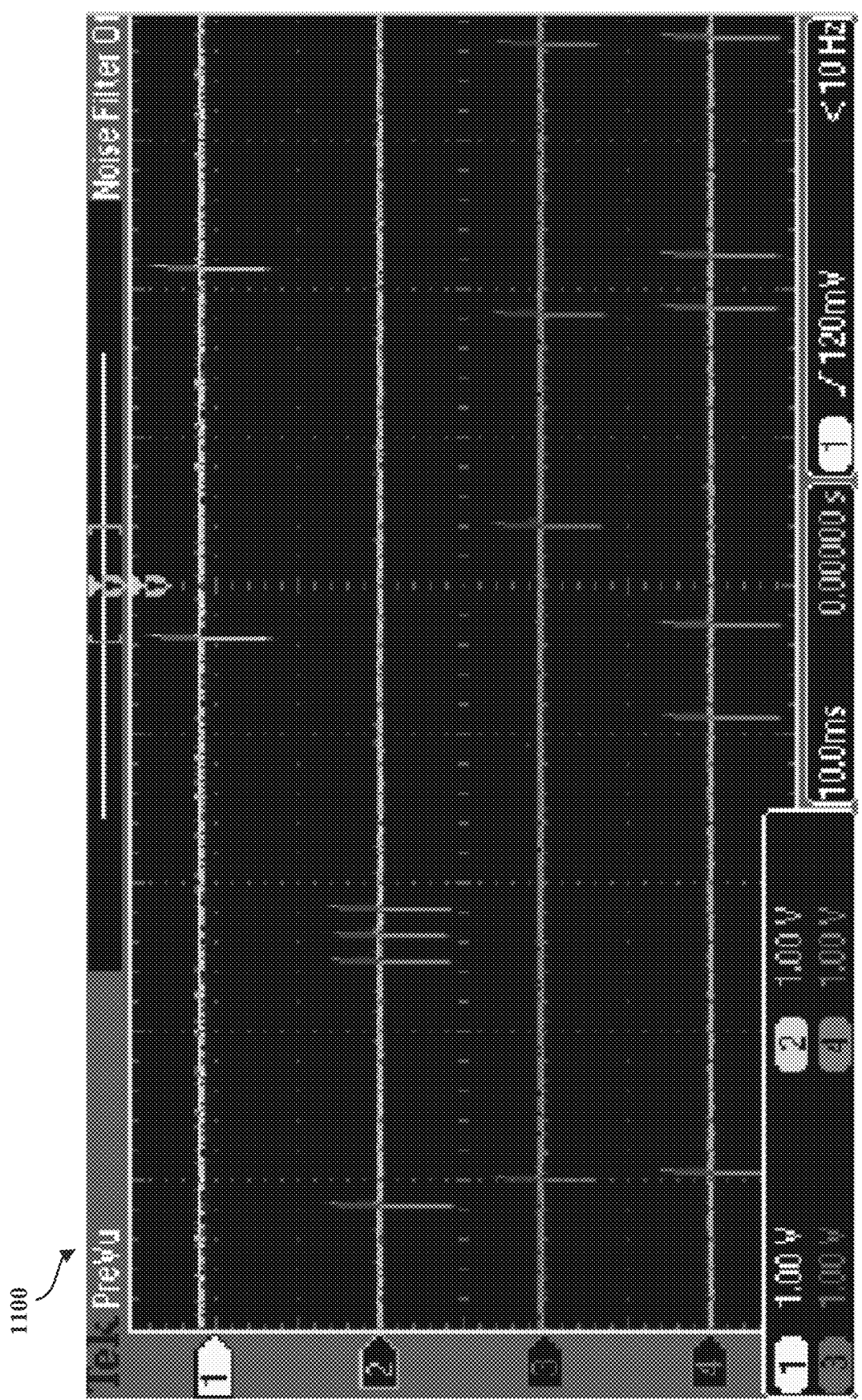
FIG. 11 is a diagram illustrating an example of biphasic pulses 1100 across four electrodes.

FIG. 11 is a diagram illustrating an example of biphasic pulses 1100 across four electrodes. The pulse trains 1102, 1104, 1106, 1108 demonstrate arbitrary spatiotemporal patterns triggered by a random number generator (RGN) produced by the microcontroller to demonstrate the arbitrary pulse generation capability of the stimulator. In FIG. 11, a sample generated output of an array of random temporal patterns from 4 selected channels is illustrated. To test stimulation and recording capability from the same electrode in PBS, we mimicked neural activity by applying a small sinusoid of 1 KHz using a function generator (FG) across a neighboring electrode from the electrode being tested. At the same time, the electrode being tested is injected with a stimulus pulse of 100 µA and 100 µs pulse width (FIG.12a).

Figure 12:
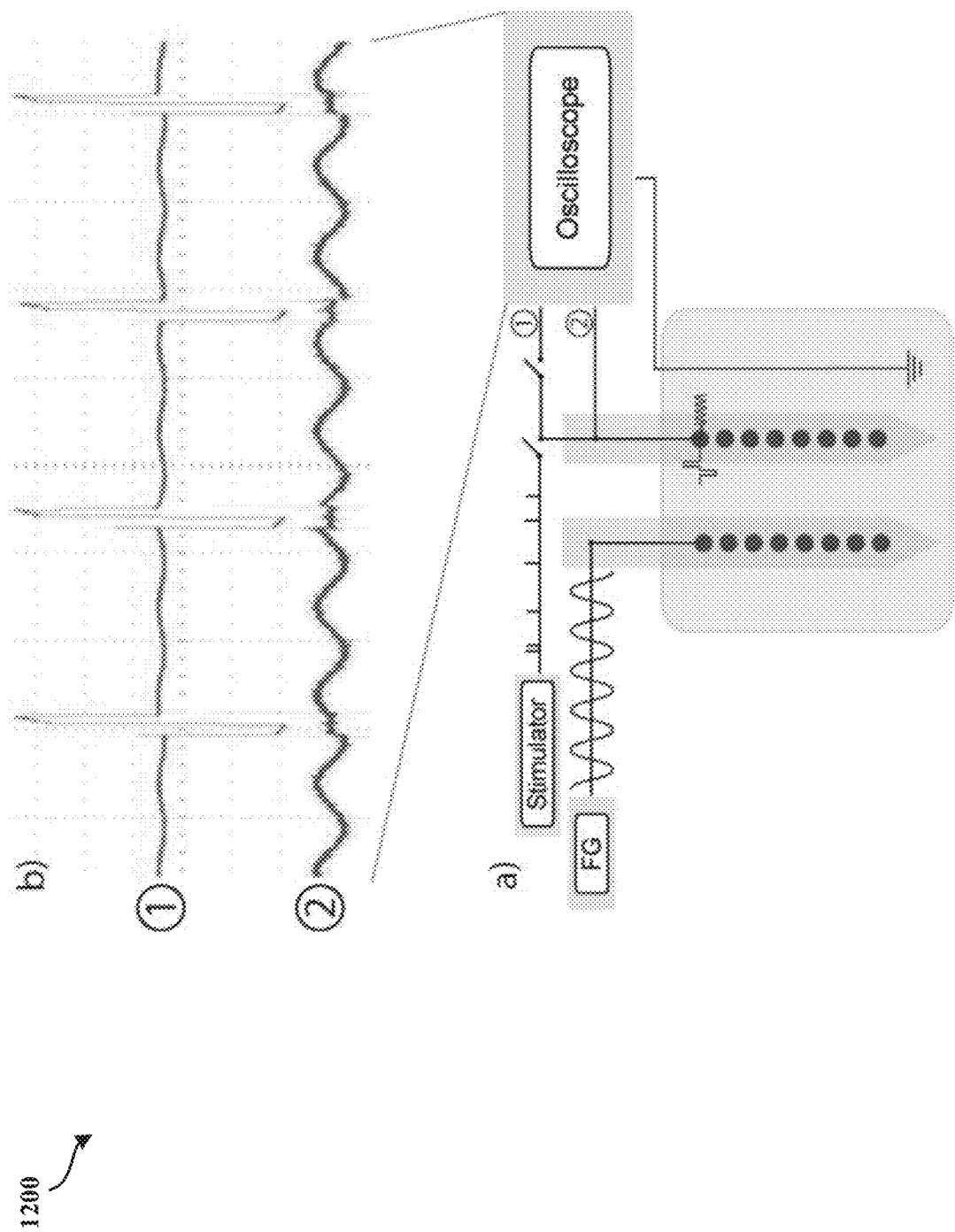
FIG. 12 is a diagram illustrating a set up to test the switching technique using a small sinusoid applied to a neighboring electrode to mimic neural tissue and the corresponding output from the oscilloscope based on the testing.

FIG. 12 is a diagram illustrating a set up to test the switching technique using a small sinusoid applied to a neighboring electrode to mimic neural tissue and the corresponding output from the oscilloscope based on the testing. As illustrated in FIG. 12, the output from the oscilloscope illustrates a lack of stimulus artifact during and at the end of the pulse. FIG. 12 demonstrates lack of stimulus artifact and the ability to resume recording 100 µs after the end of the stimulus pulse. To ensure complete stimulus artifact rejection, we tested the system across an amplifier set at 60 dB gain, 300 Hz-1 KHz band pass filter and 100 KHz sampling rate.

Figure 13:
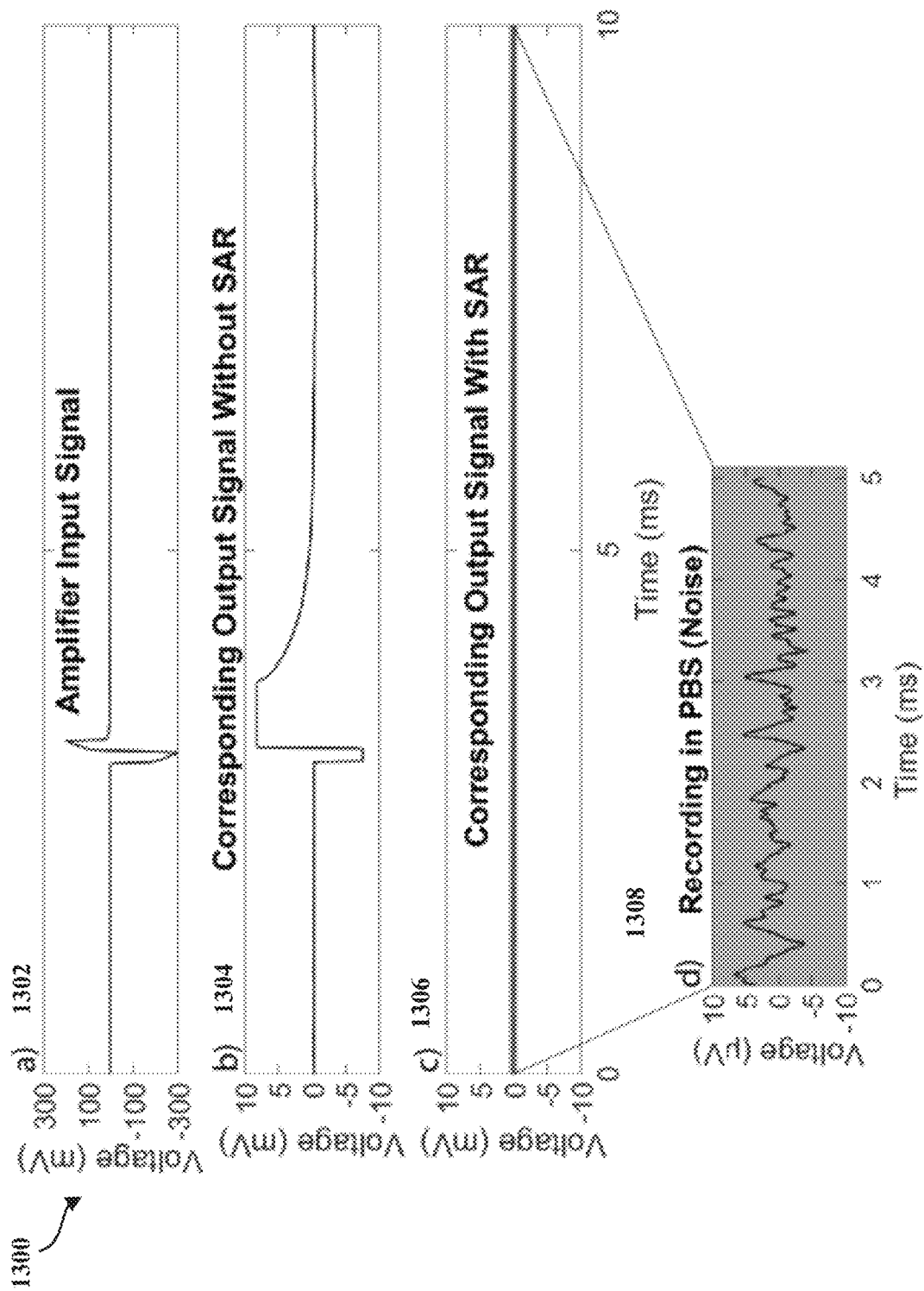
FIG. 13 is a diagram illustrating stimulation of an Iridium Oxide coated electrode in, e.g., 1×PBS with 100 μA, 100 μs biphasic and monopolar current pulse 1300.

FIG. 13 is a diagram illustrating stimulation of an Iridium Oxide coated electrode in, e.g., 1×PBS with 100 µA, 100 µs biphasic and monopolar current pulse 1300. The resultant transient voltage is illustrated at the input of the recording amplifier (1302). FIG. 13 also illustrates a corresponding stimulus artifact at the output of the recording amplifier (1304). The presented signal may be clipped (1304), and the amplifier may be saturated for ~5 ms 1304. Thus, the stimulus artifact due to the current pulse applied to the electrode in the illustrated example takes ~5 ms to fully recover (1302). FIG. 13 illustrates complete removal of the stimulus artifact using the switching technique where the amplifier is solely recording noise level voltages (1306). A complete removal of the stimulus artifact is illustrated using the described stimulus artifact rejection technique (1306). The output the amplifier is scaled by 1000× to show the input referred voltage at the amplifier. Accordingly, a zoom in on 1306 is provided to demonstrate noise level (1308).

Figure 14:
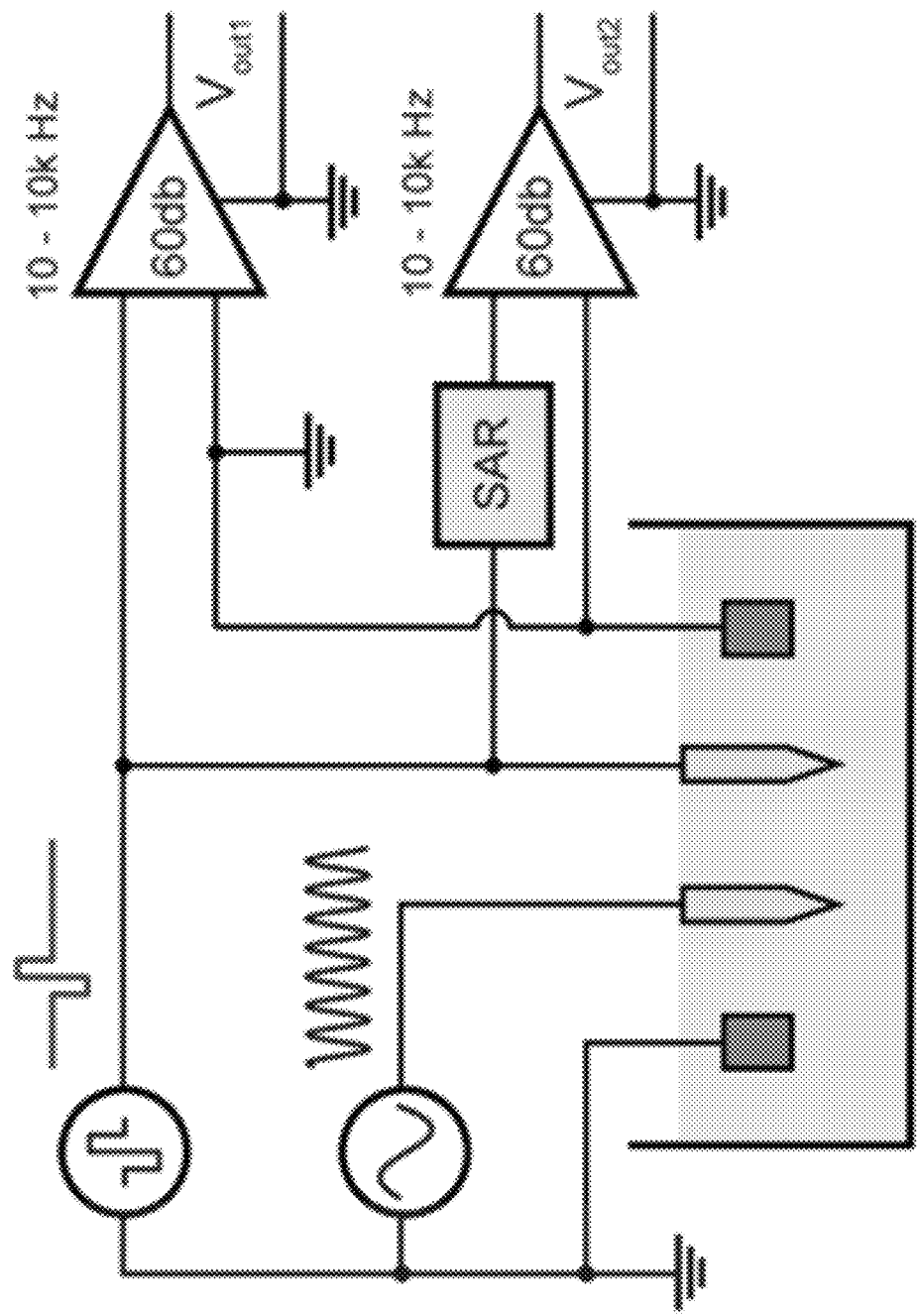
FIG. 14 is a diagram illustrating a test bench setup 1400 for evaluating the stimulus artifact with (Vout2) and without (Vout1) the SAS technique.

FIG. 14 is a diagram illustrating a test bench setup 1400 for evaluating the stimulus artifact with (Vout2) and without (Vout1) the SAS technique. The setup may include diluted PBS mimicking neural tissue and a sinusoidal signal (1 kHz, 10 mV peak to peak) applied to a neighboring electrode mimicking neural activity.

Stimulation and recording experiments were performed in a phantom to compare the artifact with and without the SAS component. The phantom was ⅙ diluted PBS mimicking brain tissue impedance of approximately 0.255/m. To mimic neural activity, a known input of 1 kHz sinusoidal signal was applied to another microelectrode in the same solution. 1 kHz was chosen because it is within the spectral range of single unit activity. Also, this frequency over the frequency of evoked potentials provides better visualization for the earliest point at which biological signals may be recovered from the stimulus artifact. The amplitude of the input sinusoid is 10 mV peak to peak (FIG. 14). The electric field from this electrode to the recording electrode would be attenuated due to distance and electrolyte impedance. This is also the case for in vivo recordings as the source of an action potential is in millivolts and distance and tissue impedance from the neuron to the recording electrode results in recordings of few hundred microvolts.

The time duration when no sinusoidal signal can be recorded due to the artifact is measured and compared. The recording amplifier used (A-M systems, model 1700) was set to 60 dB gain and a 10 Hz-10 kHz band pass filter. The maximum output voltage of this amplifier is 10V, thus the voltage at the input of the amplifier may need to be less than 10 mV to avoid saturation. All signals were digitized and recorded by a recording system (Digidata 1322A, Molecular Devices) and data were saved by pClamps9 (Molecular Devices) software using a 100 kHz sampling frequency.

Figure 15:
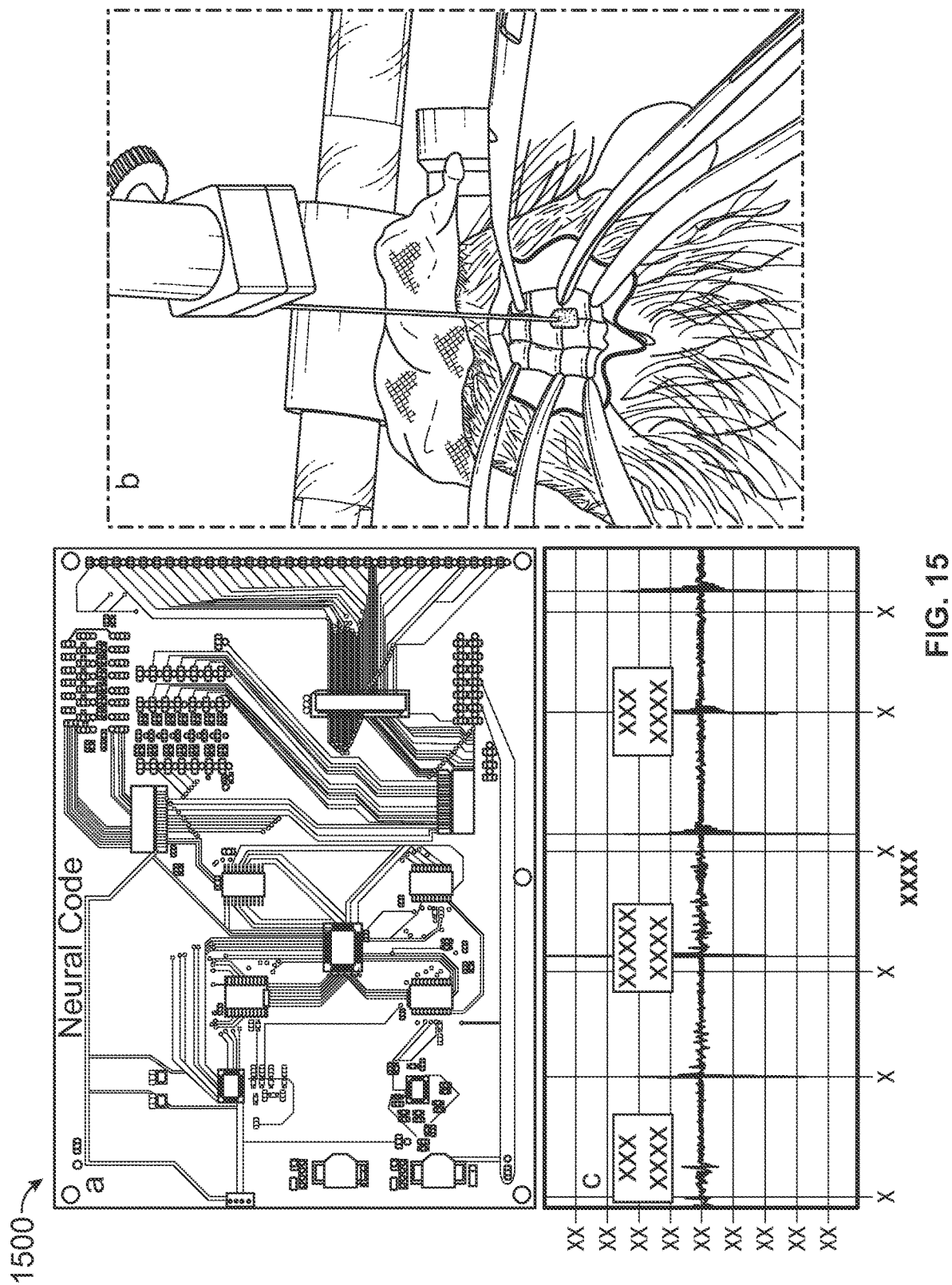
FIG. 15 is a diagram illustrating acute in vivo setup for system evaluation.

FIG. 15 is a diagram illustrating acute in vivo setup for system evaluation. (A) PCB design of the system as illustrated in FIG. 8 connected to (B) an implanted microelectrode in rat CA1 region of the hippocampus. (C) Stimulus artifacts and evoked neural responses are amplified, digitized, and saved with a bench-top neural recording system.

An in vivo evaluation was made. To demonstrate the system's functionality in vivo, microelectrode recordings were conducted in the dorsal hippocampus of one male Sprague-Dawley rat (12 weeks old, 350 g) using a designed and fabricated PCB (FIG. 15a). All procedures were performed in accordance with protocols approved by the Institutional Animal Care and Use Committee of the University of Southern California. The anesthetic induction was carried out in a vaporizer-controlled induction chamber with a mixture of 4% isoflurane and $O_2$. The rat was then anesthetized with a mixture of Ketamine and Xylazine. Once the animal was deeply anesthetized, it was placed on the surgery table. During the surgery, anesthesia was maintained with an inhalation of isoflurane (1%~2% in pure oxygen) administered with a nose cone from isoflurane machine with a scavenging cartridge attached. The status of anesthesia was checked periodically (every 15 minutes) by pinching the toe of the hind paw. If a positive "toe pinch" response was elicited, the doses of gaseous anesthesia would be increased. In addition, before, during, and after the surgical procedure, the respiratory rate, mucous membrane color, and body temperature of the rat were monitored.

Ear bars on a stereotaxic frame were used to hold the rat's head in place. A craniotomy of 2×4 mm was made over the right dorsal hippocampus and the dura was incised. The electrode was inserted at 2.80 mm posterior to the bregma and 2.50 mm lateral to the midline at a depth of 2.65 mm, perpendicular to the brain surface. A micro-manipulator was used to insert the electrode (FIG. 15b). Two reference electrodes were inserted far away from the working electrode in the hindbrain; one for the stimulator and one for the recording system.

Three sets of experiments were performed in vivo: (1) stimulate and record from the same electrode without the proposed SAS to measure the artifact, (2) stimulate and record from the same electrode with the SAS, and (3) repeat (1) and (2) after the animal is euthanized to separate neural responses from the stimulus artifacts.

A multiplexed 32-channel microstimulator has successfully been designed, fabricated, and tested. The multiplexed 32-channel microstimulator can generate an arbitrary spaciotemporal pattern of pulses driven by an external source and a stimulus artifact suppression technique for recording from the same electrodes for feedback control of stimulation parameters. System characterization including examination of asynchronous arbitrary pulse pattern generation and evaluation of stimulus artifact suppression in a phantom preparation are presented below. In vivo testing of this system on evoking and recording neural activities in the hippocampus is presented below.

Figure 16:
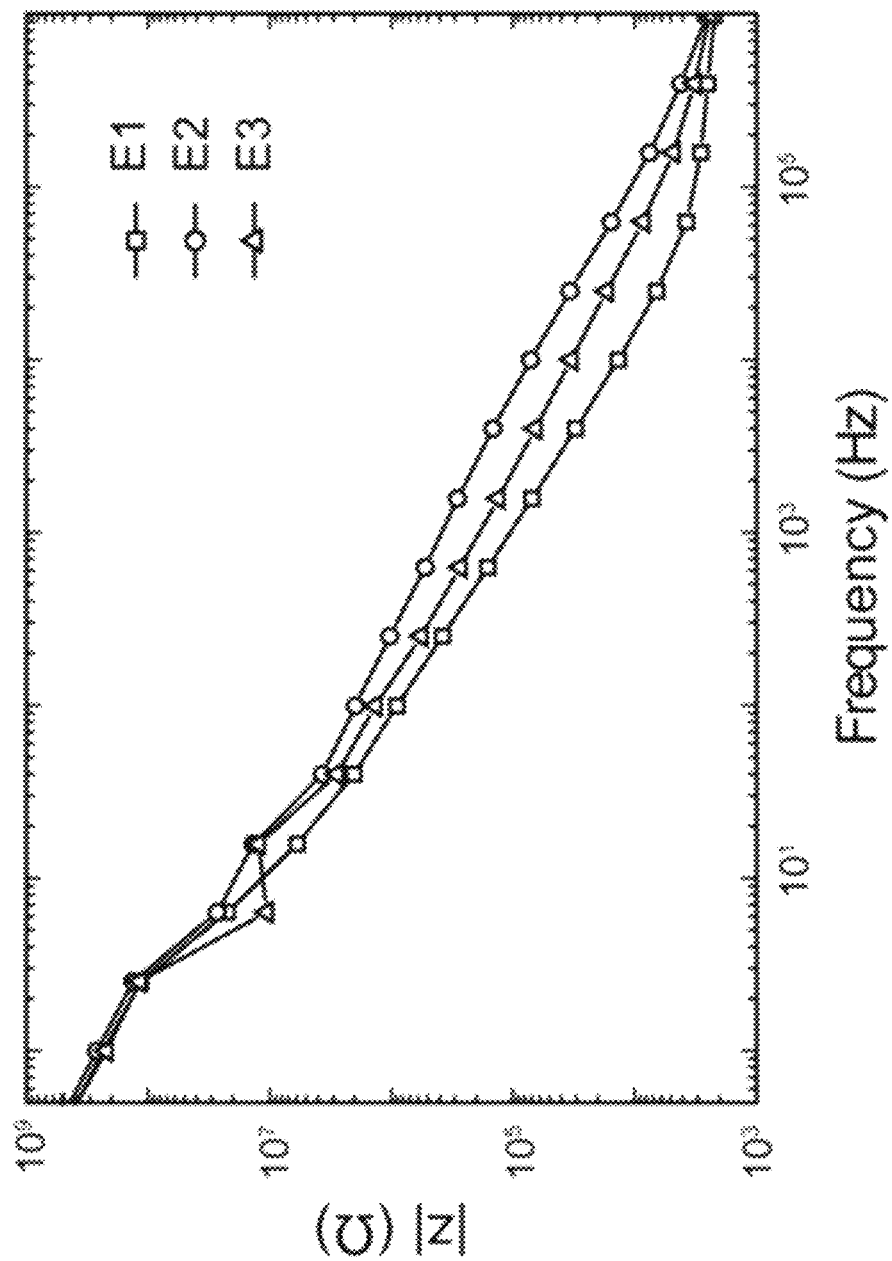
FIG. 16 is a diagram illustrating a representative electrochemical impedance spectroscopy plot of impedance magnitude in 1×PBS for three trials (E1-E3) of a Tungsten microelectrode used in all experiments.

FIG. 16 is a diagram illustrating a representative electrochemical impedance spectroscopy plot of impedance magnitude in 1×PBS for three trials (E1-E3) of a Tungsten microelectrode used in all experiments. The EIS plot of the microelectrode is presented in FIG. 16. A pulse duration of 200 μs (5 kHz) corresponds to |z| electrode of 50 kΩ. Thus, the stimuli were applied across 50 kΩ resistors, mimicking |z| electrode, with amplitudes ranging from ±1 μA to ±60 μA, and the pulse intervals ranging from 0.5 ms to 100 ms. The system can be programmed to generate cathodic or anodic first stimulation pulses across individual channels. This choice is dependent on the region of the brain being stimulated as one waveform would manifest a lower threshold than the other.

Figure 17:
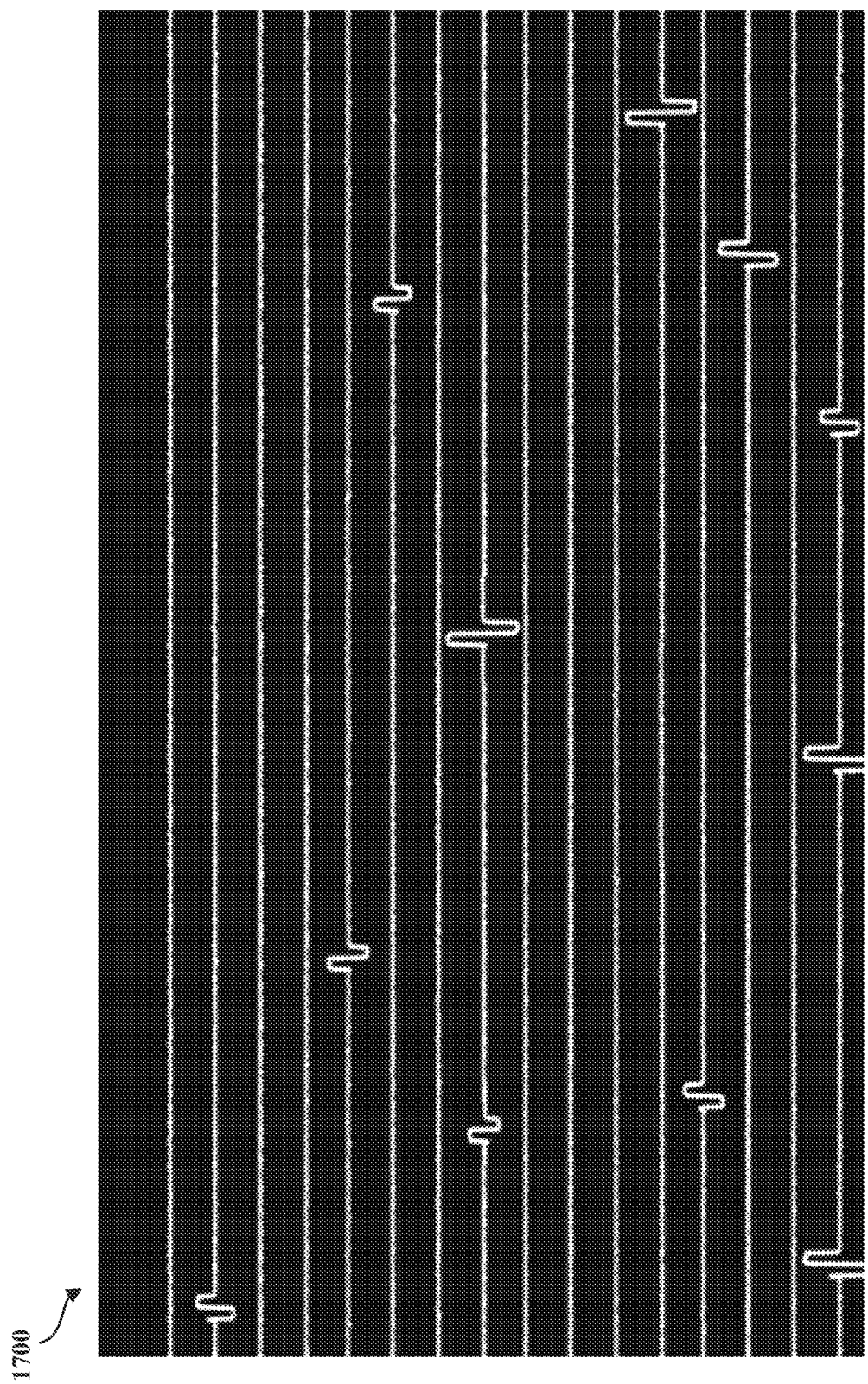
FIG. 17 is a diagram illustrating a spatiotemporal pattern of cathodic or anodic first stimulation pulses 1700 with varying amplitudes and intervals generated by the 32-channel neurostimulator.

FIG. 17 is a diagram illustrating a spatiotemporal pattern of cathodic or anodic first stimulation pulses 1700 with varying amplitudes and intervals generated by the 32-channel neurostimulator. The stimuli were applied across 50 kΩ resistors mimicking |z| electrode. The amplitudes of the pulses range from ±1 μA to ±60 μA, and the pulse intervals range from 0.5 ms to 100 ms.

The result of the arbitrary stimulation pulse generator across 32 channels is illustrated in FIG. 17 demonstrating the capability of the system to generate neural code-based stimulation with each channel generating either anodic first or cathodic first pulse. Small positive spikes at the beginning of the biphasic pulses are charge injections when switching from one channel of the mux to another. This is a value of maximum 5 pC, which is discharged during the grounding phase.

Multiplexing prevents two or more electrodes from being stimulated simultaneously. Instead, one stimulation pulse needs to be delayed by the duration of the pulse. A typical pulse duration to evoke neural response is 100-200 μs in small animals such as rats. If the pulse duration per phase is set to be 200 μs and two electrodes need to stimulate simultaneously, one pulse would be delayed by 400 μs. This is in fact rarely needed due to the sparse nature of neural spiking activities. Furthermore, the design specifications were based on hippocampal memory prosthesis applications, which uses weak stimulation pulses to activate small and localized populations of neurons. However, synchronized stimulation has also been shown effective in current steering and focusing. The example system is a 32n channel neurostimulator, where n is the number of individual current sources. Therefore, the design may easily be expanded to larger channel counts with individual current sources to allow synchronous stimulation through multiple channels.

Electrochemical Properties

CV and EIS were performed to assess the electrochemical properties of the microelectrodes used in the experiments. The measurements were analyzed with Echem Analyst (potentiostats and electrochemical instrument software by Gamry Instruments) to generate the values listed in Table 1. The cathodic charge storage capacitance of the electrode measured at a scan rate of 100 mV/s is 20 nC. The maximum charge applied to this electrode was 12 nC (60 μA*200 μs). This is below the cathodic charge storage capacity of the electrode, which is an approximation of the charge injection capacity.

TABLE 1

Electrochemical parameters of the microelectrode used in the experiments.

| $C_{dl}$ | $R_P$ | $R_S$ | Charge Storage Capacity | Time constant (τ) |
|---|---|---|---|---|
| 0.3 nF | 1 MΩ | 10 KΩ | 20 nC | 300 μs |

The Vp on the electrode after termination of the maximum stimulation pulse of 60 μA, 200 μs is 0.5V (FIG. 3*d*). After 5τ, Vp reaches to 0.5e-5=3.3 mV with respect to a large Tungsten return electrode. 5τ is chosen because the voltage across the electrode may need to reach to a value less than the input range of the amplifier to avoid saturation, which here is 10 mV. The τ of this electrode is 300 μs (Cdl*Rp), and 5τ corresponds to 1.5 ms. Thus, a duration of 1.5 ms was spent after the termination of the stimulation before the electrode is reconnected to the amplifier.

Figure 18:
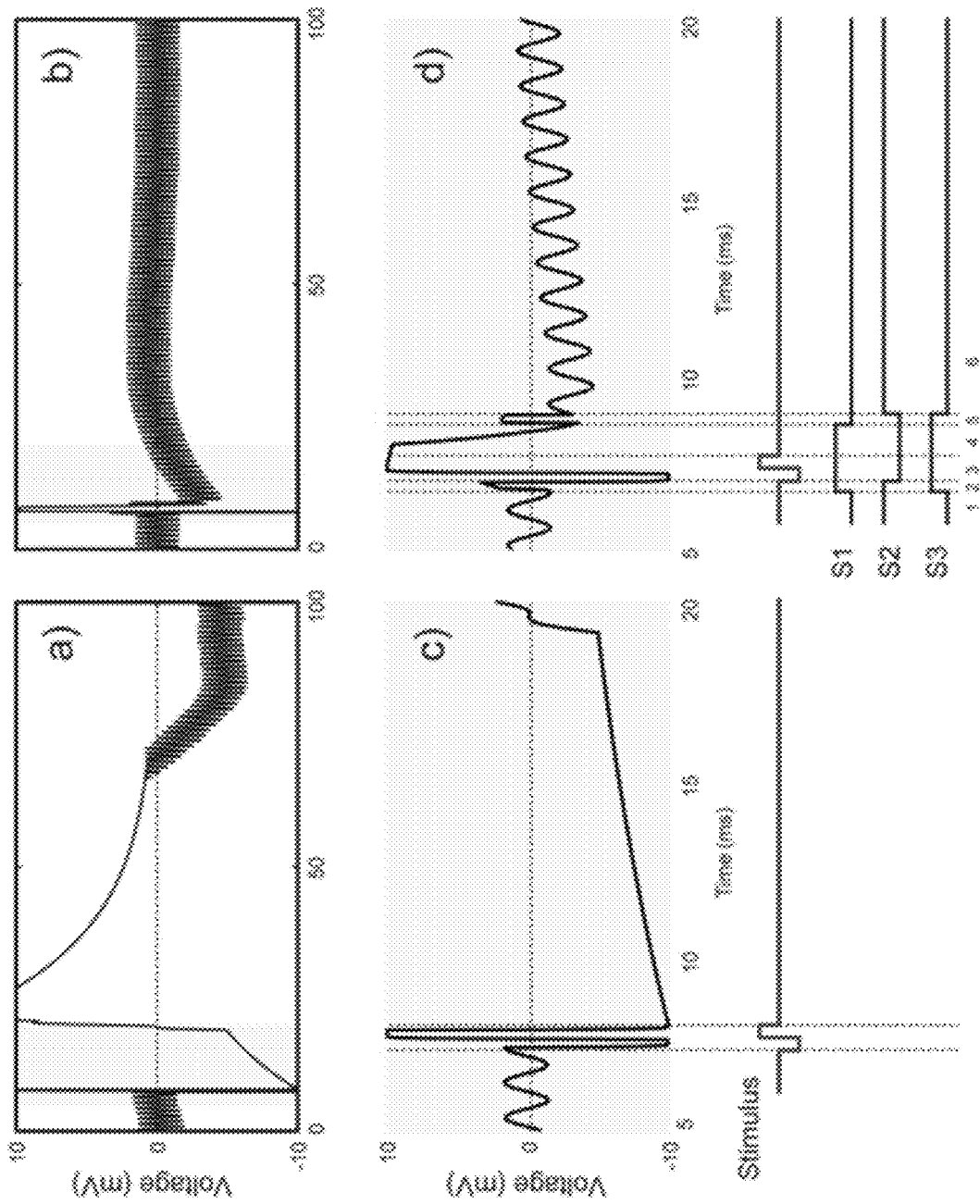
FIG. 18 is a diagram illustrating a stimulus artifact (A) without and (B) with the SAS in response to a current pulse (cathodic first, 60 µA, 200 µs)

FIG. 18 is a diagram illustrating a stimulus artifact (A) without and (B) with the SAS in response to a current pulse (cathodic first, 60 μA, 200 μs). Recording is resumed more than (A) 60 ms as opposed to (B) 2.3 ms after the onset of stimulation. (C) 15 ms time window from (A) demonstrating amplifier saturation and signal reflection. (D) 15 ms time window from (B) demonstrating the results of states 1 to 6 described in FIG. 7 and summarized as follows: 1. Recording phase, 2. switching artifact (200 μs), 3. charge coupling across S2 during stimulation (400 μs), 4. discharge period of the electrode (1.5 ms), 5. switching artifact plus residual charge across the electrode (200 μs), 6. resume recording.

FIG. 18 demonstrates the resulting stimulus artifact in a phantom preparation with and without the SAS component. The 10 mV sinusoidal input signal is attenuated and recorded at less than 1 mV by the recording electrode. The input signal takes >60 ms to recover from the stimulus artifact when the electrode is directly connected to the recording amplifier (FIG. 18*a*). By contrast, when the same signal is applied with the SAS component between the electrode and the amplifier, the recovery period is reduced to 2.3 ms (FIG. 18*b*). Based on the SNR of the recorded signal, lower amplitudes may also be detected. A 15 ms time window of the two signals is illustrated in FIGS. 18*c* and 18*d* with respect to the timing of the stimulation pulse for better visualization.

FIG. 18*c* illustrates that the stimulation pulse saturates the recording amplifier, causes ringing and finally settles according to the time constant of the electrode and the recording system. FIG. 18*d* illustrates the resulting signal with respect to the 6 states of S1-S3 illustrated in FIG. 6. State 1 is the recording phase. The artifact seen in state 2 is due to switching artifact caused by charge injection during closing of S1 and S2. State 3 illustrates the extra charge coupled from the source to the drain of S2 during stimulation, which still saturates the amplifier. The extra charge coupled is absorbed by the resistor connected at the input of the amplifier. The discharge period of the electrode is represented in state 4. The artifact in state 5 is due to switching artifact and possibly any residual charge left on the electrode when the electrode is reconnected to the amplifier. In state 6, recording is resumed but the sinusoid takes some time to recover to the baseline.

The control to compare recordings without the SAS technique is dependent on the amplifier and its settings. For example, a lower gain and higher high pass cut-off frequency will result in faster recovery period. Another factor affecting the recovery period is the input impedance of the amplifier. A lower input impedance would mean that the charge from stimulation would be divided between the electrode and the amplifier, which is undesirable. However, the settling time will be shorter and vice versa. The SAS technique is designed to be used with a variety of amplifiers. It minimizes charge coupling between the stimulator and the recording system and suppresses ringing due to amplifier saturation while using a wide-band filter.

It is apparent that the example system is not capable of stimulation and recording perfectly simultaneously. However, it is important to note that neural tissue does not instantaneously respond to the stimulation pulse. Instead, it requires a minimum amount of time termed latency to generate the evoked response. The duration of latency depends on the properties of the target excitable tissue (IRNICH 1980).

Acute in vivo Animal Validation

We stimulated the CA1 region of the hippocampus in anesthetized rats using increasing stimuli ranging in amplitude from 10 μA to 60 μA in increments of 10 μA separated in time by 1 second. Neural response was recorded with and without the SAS component. Each trial was repeated 3 times with a 5-minute recovery period between trials.

Figure 19:
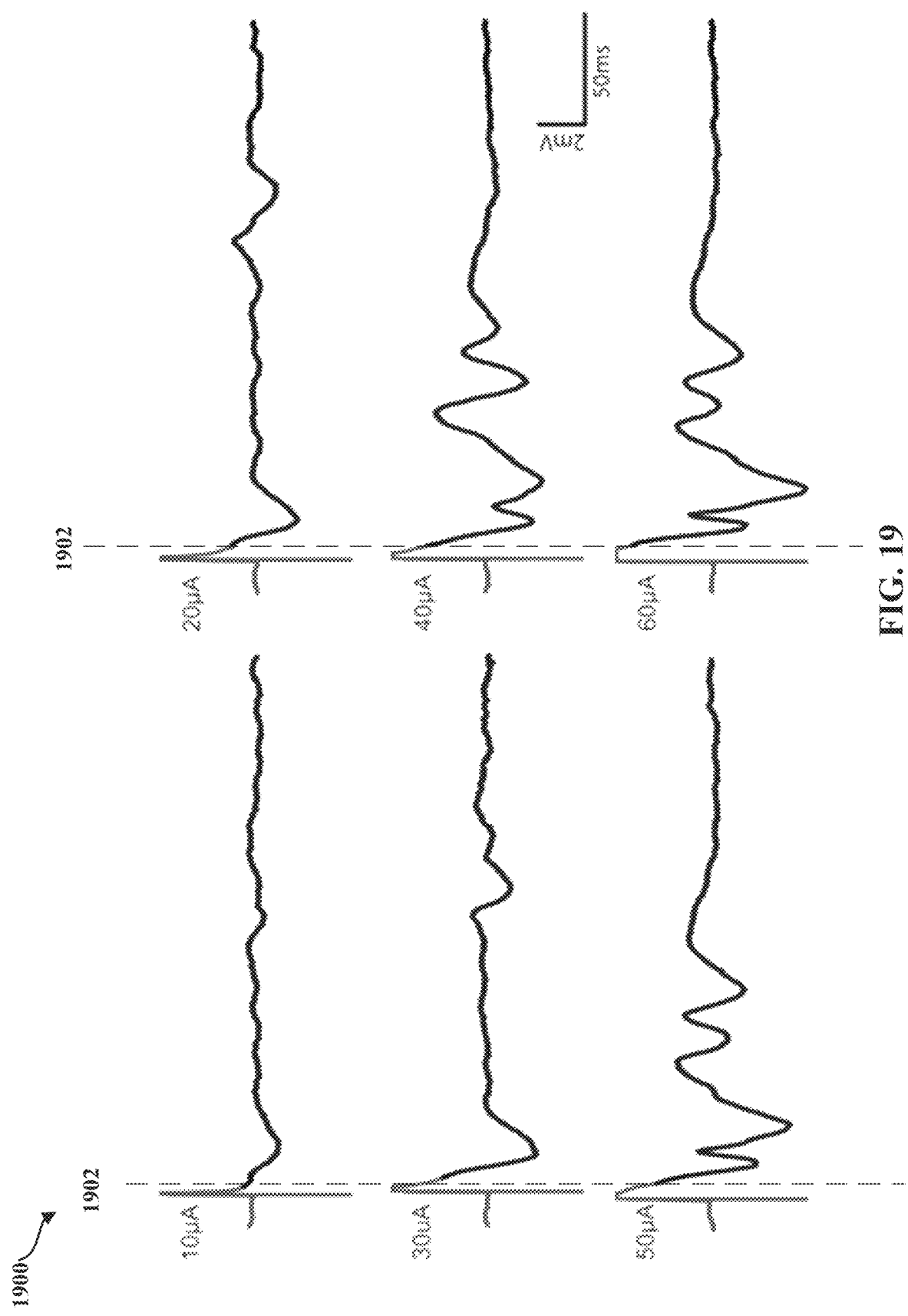
FIG. 19 is a diagram illustrating a recording of evoked neural responses to increasing micro-stimulation amplitudes in the CA1 region of the hippocampus of an anesthetized rat using the SAS component.

FIG. 19 is a diagram illustrating a recording 1900 of evoked neural responses to increasing micro-stimulation amplitudes in the CA1 region of the hippocampus of an anesthetized rat using the SAS component. All pulses are constant-current, cathodic-first and 200 μs in duration. Stimulus artifacts are during the first few milliseconds of each graph to the left of the dotted lines 1902. Evoked potentials are to the right of the dotted lines 1902. As stimulation amplitudes increase, the evoked potentials show increased amplitudes and more complex waveforms.

FIG. 19 illustrates neural responses following stimulation using the SAS component. Evoked potentials are apparent at stimulus amplitudes of 10 μA, 20 μA, and 30 μA. The amplitudes and durations of the evoked potentials increase with the stimulus amplitude. At and above 40 μA, complex waveforms with increased magnitudes are observed, possibly because more neurons are recruited, and more complex neural dynamics are elicited. The complex waveforms are characteristics of population spikes in the hippocampus as there is an initial depolarization of the nearby tissue followed by hyperpolarization deflections.

Figure 20:
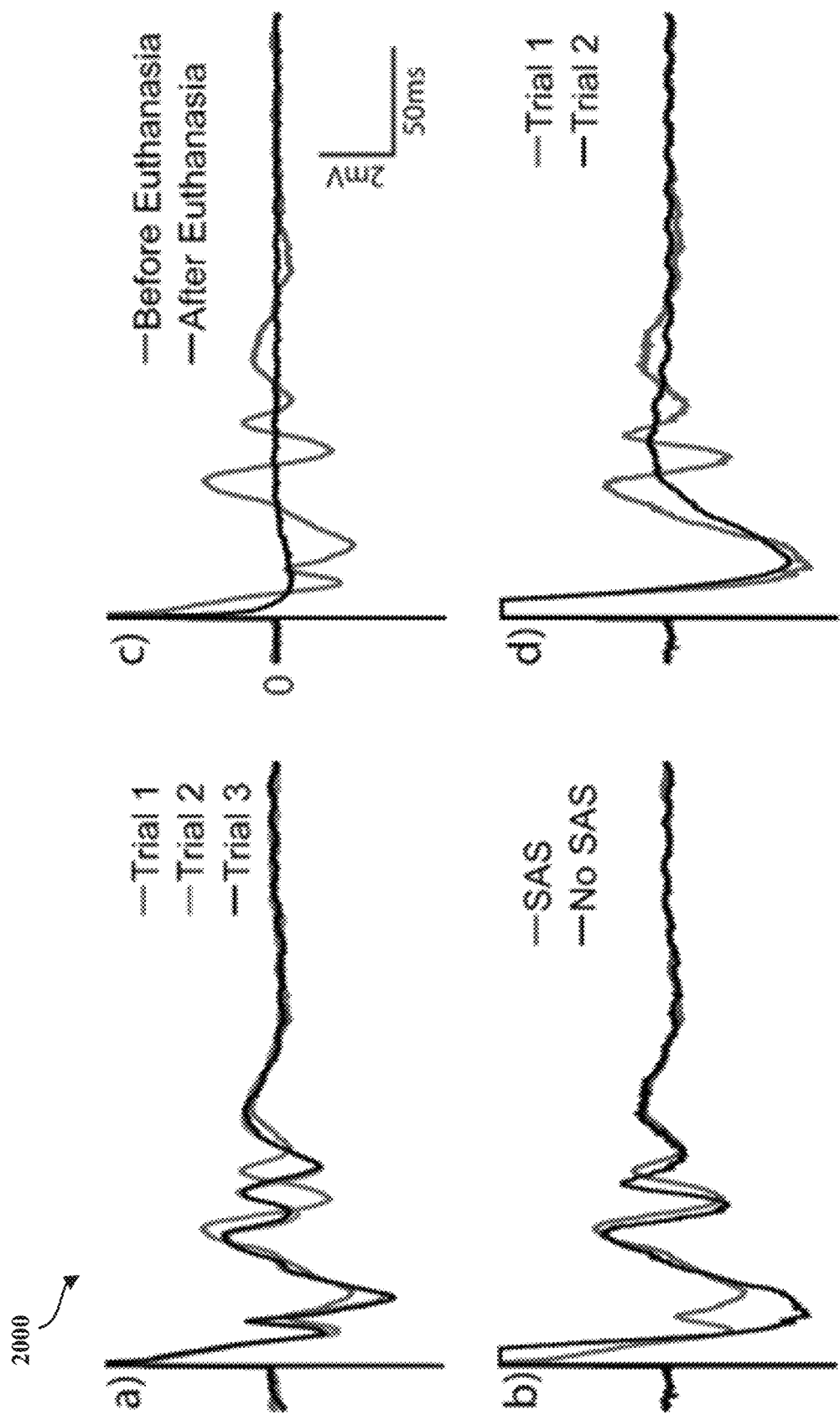
FIG. 20 is a diagram illustrating a stimulus artifacts and evoked potentials to a stimulation with 40 µA amplitude.

FIG. 20 is a diagram illustrating a stimulus artifacts and evoked potentials to a stimulation with 40 μA amplitude. (A) Three trials of recordings with the SAS. (B) Recordings with (red) and without (black) the SAS are overlaid for comparison. (C) and (D) Verification of the evoked potentials by comparing the signals before (red) and after (black) the rat was euthanized. Neural signals are retrieved within (C) ~2 ms after the stimulation onset when SAS is used, and (D) ~60 ms when SAS is not used.

FIG. 20a shows results with the SAS component. Responses from 3 trials at 40 μA stimulus are overlaid to demonstrate the repeatability and variations of the responses. Comparison of the recorded signals with and without the SAS component is demonstrated in FIG. 20b. Notably, short latency neural response is obscured when the SAS component is not used. To verify the recorded signals were indeed from neural tissue and clearly distinguish the artifact from neural activity, the experiment was repeated after the animal was euthanized as a control. Overlaying the signals recorded before and after euthanasia demonstrate clearly the effects of artifacts on the stimulating electrode with and without usage of SAS (FIG. 20 c, d).

Figure 21:
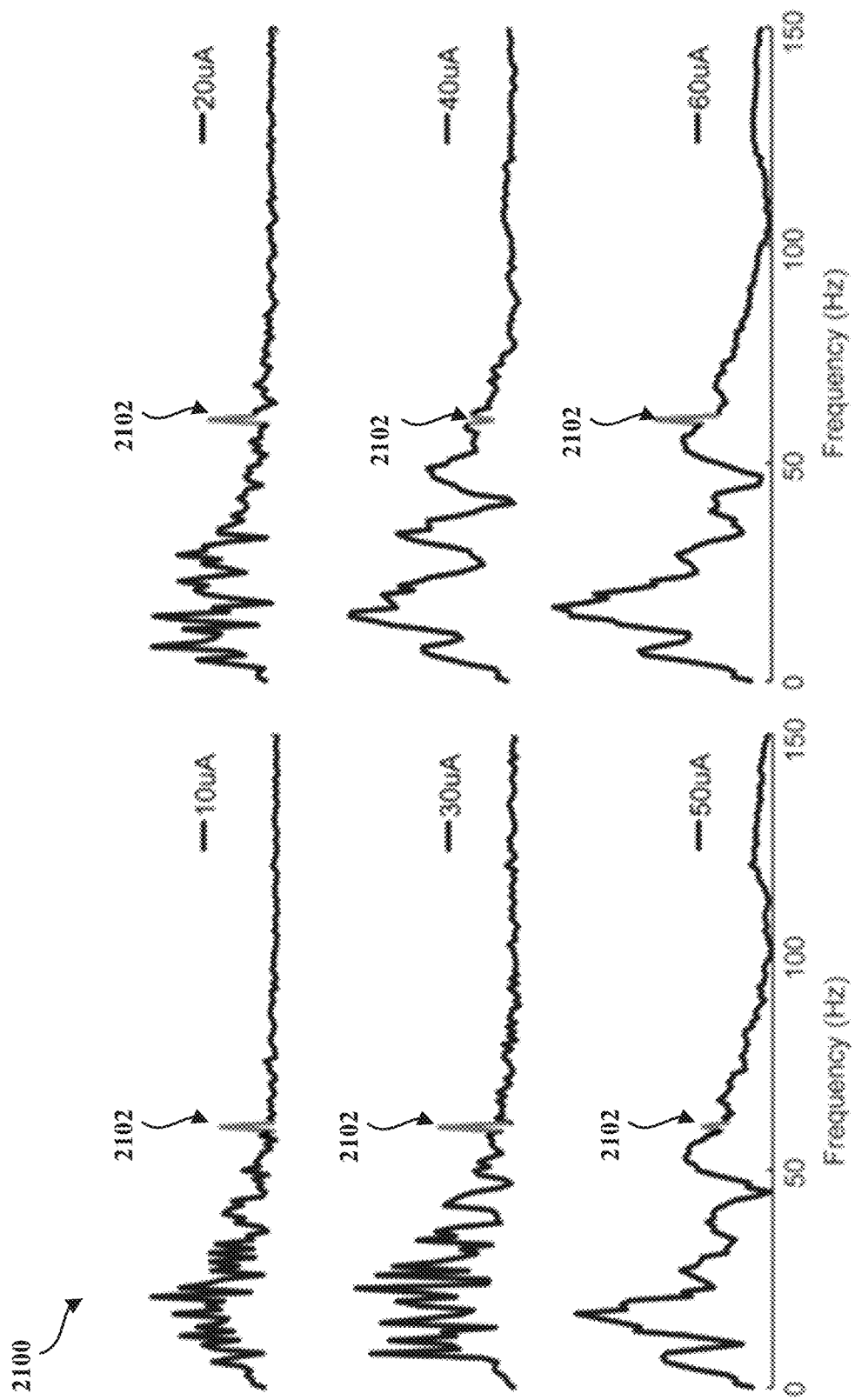
FIG. 21 is a diagram illustrating a frequency analysis of evoked potentials.

FIG. 21 is a diagram illustrating a frequency analysis of evoked potentials 2100. A 7-30 Hz band is apparent in all cases which increases in magnitude with the stimulus amplitude. Evoked potentials to higher stimulus amplitudes (40 μA, 50 μA, and 60 μA) also contain frequency components in the 40-100 Hz band. 60 Hz noise is shown at 2102.

The frequency spectrum of the evoked potentials to stimuli of 10μ, 20 μA, and 30 μA contains frequency components between 7 Hz-30 Hz. Furthermore, at higher stimulus amplitudes of 40 μA, 50 μA, and 60 μA, the neural responses also contain higher frequency components in the range of 40 Hz-100 Hz associated with Gamma oscillations previously studied in the CA1 region of the hippocampus.

Cognitive prosthesis seeks to restore cognitive function by bypassing disease or damage region of the brain. We designed and tested a versatile and inexpensive 32 channel electrical stimulation module that can be triggered to deliver highly configurable and precise pulses at any arbitrary time point defined by an external source through each independent channel continuously and in real time.

An additional unique feature in the example design is the ability to stimulate and record from the same electrode to record evoked neural activity at the end of each stimulus pulse. The benefits of this feature are that it maximizes the number of required electrodes and provides a closed-loop feedback. Monitoring neural responses in a cognitive prosthesis is important for evaluation of short latency action potentials at the site of stimulation. Another feature of the example design is the use of a multiplexer which saves power and real estate and is scalable to higher number of electrodes.

An example embodiment may provide a flexible and scalable design for use as the output unit of a cognitive prosthesis.

Future work will aim to further show the functionality of the design in vivo. A 32-channel Iridium Oxide coated electrode array will be implanted in rat hippocampus. The designed hardware will be used to send a stimulus pulse at the rate of 1-2 Hz to each electrode at random. At the same time, each electrode will be connected to a neural amplifier to simultaneously record evoke potentials.

Figure 22:
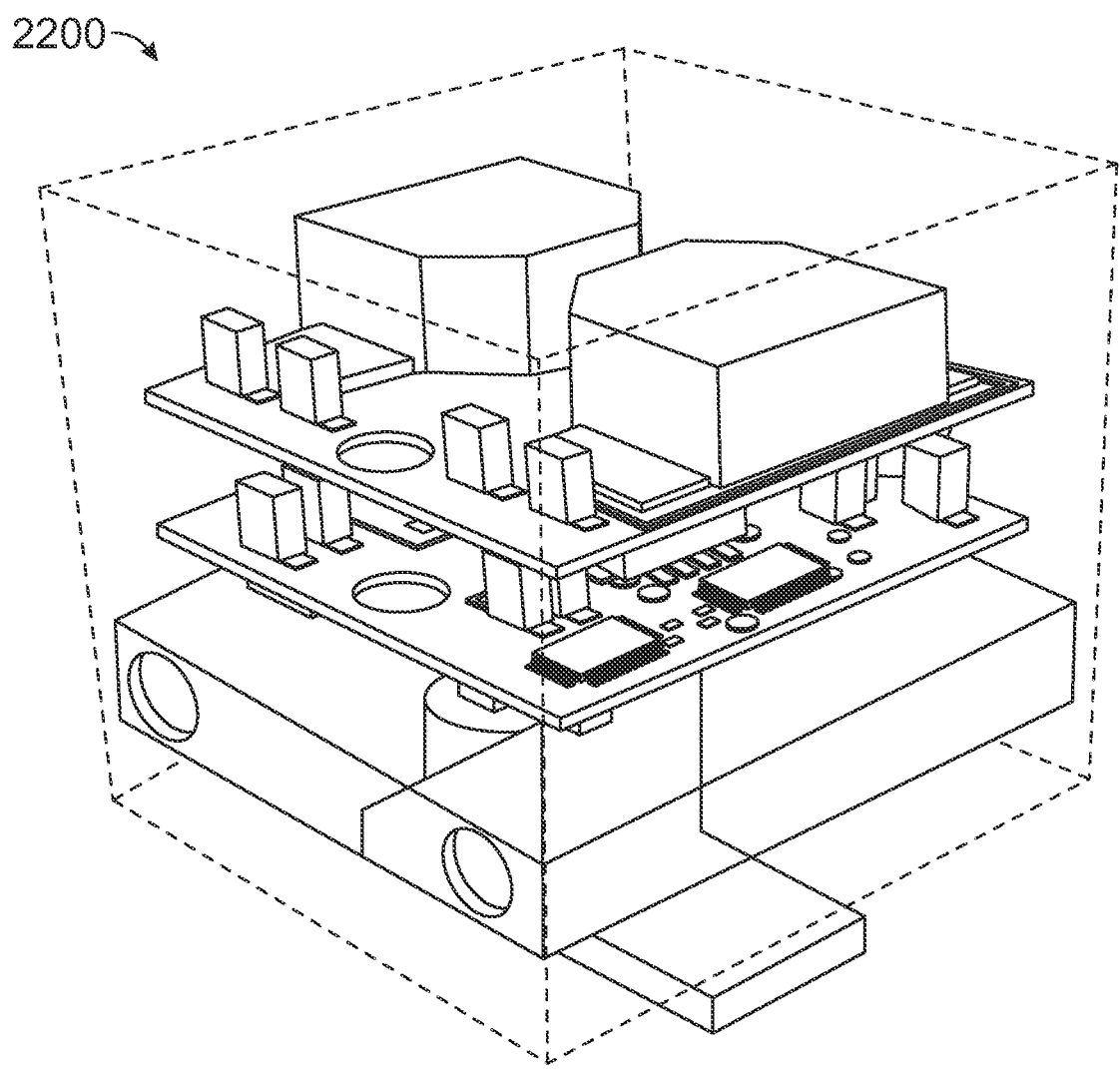
FIG. 22 is a diagram illustrating an example of miniaturize hardware for implementing the systems and methods described herein.

FIG. 22 is a diagram illustrating an example of miniaturize hardware for implementing the systems and methods described herein. The miniaturized hardware may be used on free roaming rat experiments. In the illustrated example embodiment, the layout may include a double-sided flex PCB, and a cage to mount the PCB on an animal's head. The device may provide a new tool to study brain function in animals and a step closer towards development of a cognitive prosthesis.

In an example embodiment, neurostimulator for generating neural code-based, precise, asynchronous electrical stimulation pulses is designed, fabricated and characterized. Through multiplexing, this system can deliver constant current biphasic pulses, with arbitrary temporal patterns and pulse parameters to 32 electrodes using one pulse generator. The design also features a stimulus artifact suppression technique that can be integrated with commercial amplifiers. Using an array of CMOS switches, electrodes are disconnected from recording amplifiers during stimulation, while the input of the recording system is shorted to ground through another CMOS switch to suppress ringing in the recording system. The timing of the switches used to block and suppress the stimulus artifact may be important and may be determined by the electrochemical properties of the electrode. This system allows stimulation and recording from the same electrodes to monitor local field potentials with short latencies from the region of stimulation for achieving feedback control of neural stimulation. In this way, timing between each pulse is controlled by inputs from an external source and stimulus magnitude is controlled by feed-back from neural response from the stimulated tissue. The system was implemented with low-power and compact packaged microchips to constitute an effective, cost-efficient and miniaturized neurostimulator. The device has been first evaluated in phantom preparations and then tested in hippocampi of behaving rats. Benchtop results demonstrate the capability of the stimulator to generate arbitrary spatio-temporal pattern of stimulation pulses dictated by random number generators to control magnitude and timing between each individual biphasic pulse. In vivo results show that evoked potentials elicited by the neurostimulator can be recorded ~2 ms after the termination of stimulus pulses from the same electrodes where stimulation pulses are delivered, whereas commercial amplifiers without such an artifact suppression typically result in tens to hundreds of milliseconds recovery period. This neurostimulator design is desirable in a variety of neural interface applications, particularly hippocampal memory prosthesis aiming to restore cognitive functions by reinstating neural code transmissions in the brain.

Figure 23:
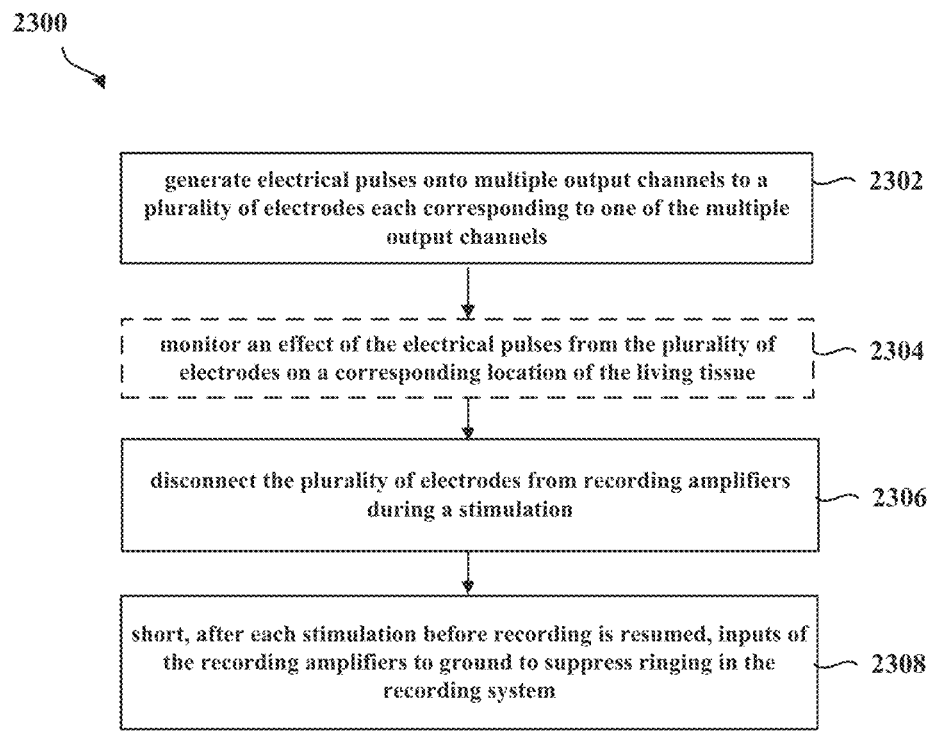
FIG. 23 is a flow diagram illustrating an example method 2300 for providing stimulation of living tissue.

FIG. 23 is a flow diagram illustrating an example method 2300 for providing stimulation of living tissue. The method includes generating electrical pulses onto multiple output channels to a plurality of electrodes each corresponding to one of the multiple output channels (2302). Generating electrical pulses may optionally include using a stimulation generator includes a single channel signal generator configured to generate the electrical pulses, and a multiplexer configured to receive the electrical pulses from the single channel signal generator and to output the electrical pulses onto the multiple output channels. Controlling operation of the multiplexer may be by transmitting control signals on select lines between a controller and the multiplexer. Optionally, the method may include monitoring an effect of the electrical pulses from the plurality of electrodes on a corresponding location of the living tissue (2304). The method also includes disconnecting the plurality of electrodes from recording amplifiers during a stimulation (2306). Additionally, the method includes shorting, after each stimulation before recording is resumed, inputs of the recording amplifiers to ground to suppress ringing in the recording system (2308). Shorting inputs of the recording amplifiers to ground may include shorting inputs of the recording amplifiers to ground through a resistor.

In an example embodiment, means for generating electrical pulses onto multiple output channels to a plurality of electrodes each corresponding to one of the multiple output channels may include a single signal generator and a multiplexer. In an example embodiment, means for disconnecting the plurality of electrodes from recording amplifiers during a stimulation may include a series of switches. In an example embodiment, mean for shorting, after each stimulation before recording is resumed, inputs of the recording amplifiers to ground to suppress ringing in the recording system may include a series of switches and resistors. In an example embodiment, means for monitoring an effect of the electrical pulses from the plurality of electrodes on a corresponding location of the living tissue return signal lines and circuitry coupled to the return signal lines for monitoring an effect of the electrical pulses. In an example embodiment, means for controlling operation of the multiplexer may include a controller and control signals on select lines between the controller and the multiplexer.

An example embodiment may deliver precise spatiotemporal patterns of stimulation pulses with arbitrary magnitudes and intervals through 32 channels continuously and in real time. The stimulator may be controlled by an external source such as a MIMO nonlinear dynamical model to achieve localized and patterned micro-stimulation to the brain. The design also may include a stimulus artifact suppression component that allows stimulation and recording from the same electrodes with a very short delay.

Highly configurable neuro-stimulators, and the ability to recording neural responses after stimulation may be used for implementing closed-loop neuromodulation or hippocampal memory prosthesis where consistent neural responses are desirable but often difficult to maintain. For example, variations in neural response may occur weeks or months after implantation due to inflammation. Inflammation causes glial cell encapsulation around the electrodes and thus weakens the neuron-electrode interaction, e.g., reduction of the stimulation effect and recorded signals. Furthermore, neural plasticity may also contribute to variations of neural responses as the underlying neural circuits are constantly altered by behaviors. These variations can be compensated by adjusting stimulation parameters based on the feedback signals provided by the recording electrodes. The systems and methods described herein may enable future studies to explore this possibility.

An example embodiment of the neurostimulator may be particularly suitable for building hippocampal memory prosthesis. In a hippocampal memory prosthesis system, spatiotemporal patterns of stimulation to a downstream brain region are calculated based on the ongoing spatiotemporal patterns of neural activities in an upstream brain region using a predictive MIMO nonlinear dynamical model. The stimulation patterns may mimic the endogenous neural signals, which intrinsically are sparse, asynchronous and involve multiple channels. The neurostimulator provides a way for delivering such patterns when connected to the output of a computational unit that contains the MIMO model.

An example embodiment may use of a multiplexer to save power and area to handle large numbers of electrodes. Higher channel counts may be achievable with hardware and software modifications, with a complexity that scales sublinearly with the channel counts. Optimum input-output ratios of the multiplexer for a hippocampal memory prosthesis may be determined. Another feature of the design is that it may use off-the-shelf microchips.

Stimulation and recording from the same electrode may be used in a hippocampal memory prosthesis. A challenge in realizing this feature is imposed by direct connection of the stimulator and amplifier through a recording electrode. When a stimulation pulse causes amplifier saturation, the input signal may be clipped at the amplifier's maximum input range. Consequently, neural response may be completely masked with this artifact and cannot be recovered. On the other hand, when recording is from a neighboring electrode to the stimulation electrode, or when the recording is from the stimulation electrode, but the applied stimulus magnitude is small enough, the amplifier may not get saturated. In this case, often back-end signal processing may be used to separate artifact from neural response.

Back-end signal processing approach may rely on unsaturated recordings of neural signals and stimulus artifacts, which may often be unavailable due to the commonly encountered saturation of recording amplifiers. Back-end signal processing of unsaturated recordings may face difficulties in separating neural activity from stimulus artifact due to their overlap in both time and frequency domains. To avoid amplifier saturation, front-end artifact reduction may be implemented, which may involve increasing the dynamic range of the amplifier to withstand larger voltages, e.g., by using a higher supply voltage. The approach may sacrifice power efficiency because of the higher supply voltage, however and may still requires back-end signal processing to reduce the stimulus artifact. Another front-end approach is to subtract the artifact at the negative input of the amplifier based on a model that replicates the electrode-tissue properties. This technique may involve relatively complex computation and may need to be validated in biological preparations.

Blanking techniques similar to the example system have previously been used to reduce the artifact recorded from non-stimulation electrodes, where residual charge left on the electrode after termination of the stimulation pulse does not need to be accounted for. Some systems may account for the discharge period of the stimulation electrode for same electrode stimulating and recording. This system does not demonstrate data from bench-top system or neural tissue. Hottowy et al. (Hottowy et al. 2012) designed a system with capability to generate spatio-temporal pattern of stimulation and stimulus artifact reduction. The range of stimuli used in this system to test the artifact rejection technique in vitro are low (0.43 µA, 100 µs), which did not cause amplifier saturation.

An example embodiment may be capable of recording and stimulating from the same electrode when a large stimulus of 60 µA, 200 µs are applied to the electrode. A large stimulus may saturate the amplifier and causes ringing for tens to hundreds of milliseconds depending on the time constant of the electrode and the input impedance of the amplifier. To minimize charge coupling between the stimulator and the amplifier, prevent ringing, and allow discharge of the stimulation electrode, some example embodiments describe the electrochemical characterization of the electrode to determine switch timing.

An example embodiment may use smaller electrodes to record evoked response, as well as, spike trains. To make the electrodes suitable for stimulation and recording spike activities, we will use Pt—Ir electroplated electrodes which have shown to increase charge storage capacity without increasing the geometric area of the electrode. An example embodiment may be fully closed-loop by using real-time analysis of neural response to stimulation for use as input to the example system for online adjustment of stimulation magnitude.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A system for providing stimulation of living tissue, the system comprising:
   a de-multiplexer control unit for receiving a plurality of sequences of temporal electrical pulses and for generating a plurality of control signals based on the plurality of sequences of temporal electrical pulses;
   a stimulation generator configured to generate a signal on a single channel, the signal comprising a sequence of temporal electrical pulses based on the plurality of sequences of temporal electrical pulses, each one of the plurality of sequences of temporal electrical pulses corresponding to a spatial location and a channel of a plurality of spatial channels;
   a de-multiplexer for receiving the sequence of temporal electrical pulses and the plurality of control signals and for generating a reconstructed plurality of sequences of temporal electrical pulses on a plurality of output channels based on the sequence of temporal electrical pulses and based on the plurality of control signals from the de-multiplexer control unit; and a plurality of electrodes each corresponding to one of the plurality of output channels, wherein each of the plurality of output channels, and each associated electrode of the plurality of electrodes, is associated with a different spatial location on the living tissue.

2. The system of claim 1, further comprising:
a recording module configured to monitor an effect of the reconstructed plurality of sequences of temporal electrical pulses from the plurality of electrodes on a corresponding location of the living tissue; and
a second plurality of switches each located between a respective one of the plurality of electrodes and the recording module.

3. The system of claim 2, further comprising a first plurality of switches each located between a respective one of the plurality of output channels and a corresponding electrode of the plurality of electrodes, and further comprising a controller coupled to the first plurality of switches and the second plurality of switches and configured to control a first switch of the first plurality of switches to be closed and to control at least a second switch of the second plurality of switches to be open when an electrical pulse of the sequence of temporal electrical pulses is transmitted on the corresponding electrode, wherein the corresponding electrode corresponds to the first switch and the second switch.

4. The system of claim 3, wherein the controller is further configured to control all of the first plurality of switches and all of the second plurality of switches to be open except for the first switch when the reconstructed plurality of sequences of temporal electrical pulses are transmitted across the first switch to the corresponding electrode.

5. The system of claim 3, wherein the controller is further configured to control the first plurality of switches to be open and the second plurality of switches to be closed after the reconstructed plurality of sequences of temporal electrical pulses has been transmitted across the first switch.

6. The system of claim 3, further comprising a circuit element having a first terminal coupled between the second switch and the recording module, and a second terminal coupled to a ground.

7. The system of claim 6, wherein the circuit element is a resistor.

8. The system of claim 3, further comprising a circuit element configured to create a short to a ground between the corresponding electrode and the ground to reduce charge buildup at the corresponding electrode.

9. The system of claim 8, wherein the circuit element is configured to create the short to the ground after any one of the reconstructed plurality of sequences of temporal electrical pulses have been transmitted across the first switch.

10. A method for providing spatiotemporal stimulation of living tissue, the method comprising:
generating, at a de-multiplexer control unit, a plurality of control signals based ona plurality of sequences of temporal electrical pulses;

generating, at a stimulation generator, a sequence of temporal electrical pulses based on input from the plurality of sequences of temporal electrical pulses, each one of the plurality of sequences of temporal electrical pulses corresponding to a spatial location and a channel of a plurality of spatial channels;

generating, at a de-multiplexer, a reconstructed plurality of sequences of temporal electrical pulses onto a plurality of output channels based on the sequence of temporal electrical pulses and based on the plurality of control signals from the de-multiplexer control unit, wherein each of the plurality of output channels is associated with a corresponding one of a plurality of electrodes;

disconnecting the plurality of electrodes from recording amplifiers during a stimulation; and shorting, after each stimulation before recording is resumed, inputs of the recording amplifiers to ground to suppress ringing in a recording module.

11. The method of claim 10, further comprising monitoring an effect of the reconstructed plurality of sequences of temporal electrical pulses from the plurality of electrodes on a corresponding location of the living tissue.

12. The method of claim 10, wherein generating electrical pulses includes using a single channel signal generator configured to generate the sequence of temporal electrical pulses.

13. The method of claim 10, wherein shorting inputs of the recording amplifiers to ground comprises shorting inputs of the recording amplifiers to ground through a resistor.

14. A system for providing stimulation of living tissue, the system comprising:
means for generating a plurality of control signals based on a plurality of sequences of temporal electrical pulses;
means for generating a sequence of temporal electrical pulses based on input from the plurality of sequences of temporal electrical pulses, each one of the plurality of sequences of temporal electrical pulses corresponding to a spatial location and a channel of a plurality of spatial channels, and for generating a reconstructed plurality of sequences of temporal electrical pulses onto a plurality of output channels based on the sequence of temporal electrical pulses, wherein each of the plurality of output channels is associated with a corresponding one of a plurality of electrodes;
means for disconnecting the plurality of electrodes from recording amplifiers during a stimulation; and
means for shorting, after each stimulation before recording is resumed, inputs of the recording amplifiers to ground to suppress ringing in a recording module.

15. The system of claim 14, wherein the recording module is configured for monitoring an effect of the reconstructed plurality of sequences of temporal electrical pulses from the plurality of electrodes on a corresponding location of the living tissue.

16. The system of claim 14, wherein the means for shorting inputs of the recording amplifiers to ground comprises a resistor.

* * * * *